US012337105B2

(12) United States Patent
Jones et al.

(10) Patent No.: US 12,337,105 B2
(45) Date of Patent: *Jun. 24, 2025

(54) AEROSOLIZATION USING TWO AEROSOL GENERATORS

(71) Applicant: IMPERIAL TOBACCO LIMITED, Bristol (GB)

(72) Inventors: David Jones, Liverpool (GB); Chris Lord, Liverpool (GB); Thomas Sudlow, Liverpool (GB)

(73) Assignee: IMPERIAL TOBACCO LIMITED, Bristol (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/733,777

(22) Filed: Jun. 4, 2024

(65) Prior Publication Data

US 2024/0325662 A1    Oct. 3, 2024

Related U.S. Application Data

(63) Continuation of application No. 18/191,820, filed on Mar. 28, 2023, now Pat. No. 12,029,846, which is a
(Continued)

(30) Foreign Application Priority Data

Sep. 22, 2017 (GB) ...................... 1715386

(51) Int. Cl.
*A24F 40/48* (2020.01)
*A24F 40/30* (2020.01)
(Continued)

(52) U.S. Cl.
CPC ............ *A61M 15/06* (2013.01); *A24F 40/30* (2020.01); *A24F 40/48* (2020.01); *A24F 40/485* (2020.01);
(Continued)

(58) Field of Classification Search
CPC ................................ A24F 40/48; A61M 15/06
See application file for complete search history.

(56) References Cited

U.S. PATENT DOCUMENTS

| 3,014,844 A | 12/1961 | Thiel et al. |
| 4,184,496 A | 1/1980 | Adair |

(Continued)

FOREIGN PATENT DOCUMENTS

| CN | 203168036 | 9/2013 |
| CN | 106235420 A | 12/2016 |

(Continued)

OTHER PUBLICATIONS

Combined Search and Examination Report for U.K. Appl. No. GB1715386.7; Date of Mailing: Mar. 22, 2018; 7 pages.

(Continued)

*Primary Examiner* — Neil Abrams
(74) *Attorney, Agent, or Firm* — Perkins Coie LLP; Kenneth H. Ohriner

(57) ABSTRACT

An aerosol delivery device includes a first aerosol generator to generate a first aerosol from a first aerosol precursor and to introduce the first aerosol into a first fluid flow pathway, and a second aerosol generator to generate a second aerosol from a second aerosol precursor and to introduce the second aerosol into a second fluid flow pathway. The first aerosol is sized for pulmonary penetration. The second aerosol generator comprises a Venturi aperture to dispense and aerosolise the second aerosol precursor in the second aerosol generator. The second aerosol precursor is a liquid, and the second aerosol is sized to inhibit pulmonary penetration. The second aerosol is transmissible within a mammalian oral and/or nasal cavity. The second aerosol includes an active
(Continued)

component for activating at least one of: one or more taste receptors in the oral cavity and one or more olfactory receptors in the nasal cavity.

20 Claims, 12 Drawing Sheets

Related U.S. Application Data continuation of application No. 16/648,483, filed as application No. PCT/EP2018/075697 on Sep. 21, 2018, now Pat. No. 11,633,556.

(51) Int. Cl.
| | | |
|---|---|---|
| *A24F 40/485* | (2020.01) | |
| *A61M 11/04* | (2006.01) | |
| *A61M 15/06* | (2006.01) | |
| *A24F 40/10* | (2020.01) | |
| *A61M 15/00* | (2006.01) | |

(52) U.S. Cl.
CPC .......... *A61M 11/042* (2014.02); *A24F 40/10* (2020.01); *A61M 15/0085* (2013.01); *A61M 2205/0294* (2013.01); *A61M 2205/8206* (2013.01); *A61M 2206/14* (2013.01); *H05B 2203/021* (2013.01)

(56) References Cited

U.S. PATENT DOCUMENTS

| | | | |
|---|---|---|---|
| 4,284,089 A | 8/1981 | Ray | |
| 4,765,347 A | 8/1988 | Sensabaugh, Jr. et al. | |
| 4,774,971 A | 10/1988 | Vieten | |
| 4,945,929 A | 8/1990 | Egilmex | |
| 5,101,838 A | 4/1992 | Schwartz et al. | |
| 5,137,034 A | 8/1992 | Perfetti et al. | |
| 5,628,984 A | 5/1997 | Boucher | |
| 6,216,705 B1 | 4/2001 | Ossepian | |
| 6,234,167 B1 | 5/2001 | Cox | |
| 9,888,719 B2 | 2/2018 | Cadieux | |
| 10,368,581 B2 * | 8/2019 | Rostami | H04L 65/1069 |
| 10,426,197 B2 | 10/2019 | Thorens | |
| 10,645,970 B2 | 5/2020 | Borkovec et al. | |
| 10,932,492 B2 | 3/2021 | Zinovik | |
| 10,952,471 B2 | 3/2021 | Batista et al. | |
| 11,090,450 B2 | 8/2021 | Li et al. | |
| 11,116,919 B2 | 9/2021 | Buchberger | |
| 11,559,085 B2 | 1/2023 | Fujinaga | |
| 11,633,556 B2 * | 4/2023 | Jones | A61M 11/042 131/328 |
| 12,029,846 B2 * | 7/2024 | Jones | B05B 17/0638 |
| 12,114,694 B2 * | 10/2024 | Bruton | A24F 40/485 |
| 2002/0170566 A1 | 11/2002 | Farr | |
| 2002/0179102 A1 | 12/2002 | Farr | |
| 2003/0234297 A1 | 12/2003 | Bloom | |
| 2006/0207596 A1 | 9/2006 | Lane | |
| 2007/0248548 A1 | 10/2007 | Blondino et al. | |
| 2007/0267032 A1 | 11/2007 | Shan | |
| 2008/0092912 A1 | 4/2008 | Robinson et al. | |
| 2010/0124535 A1 | 5/2010 | Loxley et al. | |
| 2011/0094523 A1 | 4/2011 | Thorens | |
| 2012/0111346 A1 | 5/2012 | Rinker et al. | |
| 2012/0318882 A1 | 12/2012 | Abehasera | |
| 2013/0192615 A1 | 8/2013 | Tucker et al. | |
| 2014/0261488 A1 | 9/2014 | Tucker | |
| 2014/0332014 A1 | 11/2014 | Penrose | |
| 2014/0209105 A1 | 12/2014 | Sears et al. | |
| 2015/0122276 A1 | 5/2015 | Johnson | |
| 2015/0257447 A1 | 9/2015 | Sullivan | |
| 2015/0283070 A1 | 10/2015 | Stenzler et al. | |
| 2015/0374035 A1 | 12/2015 | Sanchez | |
| 2015/0374938 A1 | 12/2015 | Scheiber et al. | |
| 2016/0044966 A1 | 2/2016 | Li | |
| 2016/0058959 A1 | 3/2016 | Hearn | |
| 2016/0081394 A1 | 3/2016 | Alarcon et al. | |
| 2016/0089508 A1 | 3/2016 | Smith | |
| 2016/0135506 A1 | 5/2016 | Sanchez et al. | |
| 2016/0213065 A1 | 7/2016 | Wensley et al. | |
| 2016/0213866 A1 | 7/2016 | Tan | |
| 2016/0228658 A1 | 8/2016 | Minskoff | |
| 2016/0262456 A1 | 9/2016 | Borkovec et al. | |
| 2016/0262457 A1 | 9/2016 | Borkovec et al. | |
| 2016/0324216 A1 | 11/2016 | Li et al. | |
| 2016/0330999 A1 | 11/2016 | Cameron | |
| 2017/0071249 A1 | 3/2017 | Ampolini et al. | |
| 2017/0157341 A1 | 6/2017 | Pandya et al. | |
| 2017/0251722 A1 | 9/2017 | Kobal et al. | |
| 2017/0251723 A1 | 9/2017 | Kobal et al. | |
| 2017/0354184 A1 | 12/2017 | Mironov | |
| 2017/0360093 A1 | 12/2017 | Fernando | |
| 2018/0007966 A1 | 1/2018 | Li et al. | |
| 2018/0027875 A1 | 2/2018 | Rostami et al. | |
| 2018/0027882 A1 | 2/2018 | Hepworth et al. | |
| 2018/0042308 A1 | 2/2018 | Takeuchi | |
| 2018/0170566 A1 | 6/2018 | Paolini et al. | |
| 2018/0304283 A1 | 10/2018 | Kazuaki | |
| 2020/0230333 A1 | 7/2020 | Jones et al. | |
| 2020/0275702 A1 * | 9/2020 | Mironov | A24F 40/46 |
| 2021/0235769 A1 | 8/2021 | Marubashi | |
| 2022/0287361 A1 | 9/2022 | Kim | |
| 2023/0030615 A1 | 2/2023 | Jang | |
| 2023/0292839 A1 | 9/2023 | Kim | |

FOREIGN PATENT DOCUMENTS

| | | |
|---|---|---|
| CN | 205987968 U | 3/2017 |
| EP | 0295122 | 1/1992 |
| EP | 3097803 | 11/2016 |
| EP | 3135136 | 3/2017 |
| EP | 3135138 | 3/2017 |
| EP | 3158883 B8 | 4/2017 |
| GB | 2032244 B9 | 5/1980 |
| GB | 2115676 | 7/1985 |
| GB | 2529727 | 3/2016 |
| GB | 2536306 | 9/2016 |
| GB | 2536307 | 9/2016 |
| GB | 2542404 | 3/2017 |
| GB | 2556331 | 5/2018 |
| GB | 2553136 | 9/2020 |
| JP | 1990-171174 A | 7/1990 |
| JP | 2007-511437 A | 5/2007 |
| JP | 2015-506182 A | 3/2015 |
| JP | 2016-215134 A | 12/2016 |
| KR | 20-2014-0002296 U | 4/2014 |
| RU | 2446895 | 4/2012 |
| RU | 2551311 | 5/2015 |
| RU | 2613785 | 3/2017 |
| RU | 201514686 | 6/2017 |
| WO | 2005049449 | 6/2005 |
| WO | 2013000967 | 6/2012 |
| WO | 2013083638 | 6/2013 |
| WO | 2013133903 | 9/2013 |
| WO | 2013178769 | 12/2013 |
| WO | 2014012907 | 1/2014 |
| WO | 2014140273 | 9/2014 |
| WO | 2014150131 | 9/2014 |
| WO | 2014187770 A2 | 11/2014 |
| WO | 2015013109 | 1/2015 |
| WO | 2015112750 | 7/2015 |
| WO | 2015179388 | 11/2015 |
| WO | 2016050244 | 4/2016 |
| WO | 2016050245 | 4/2016 |
| WO | 2016062777 | 4/2016 |
| WO | 2016096497 | 6/2016 |
| WO | 2016124740 | 8/2016 |
| WO | 2016135331 | 9/2016 |
| WO | 2016135342 | 9/2016 |
| WO | 2017015303 | 1/2017 |
| WO | 2017032695 | 3/2017 |
| WO | 2017068101 | 4/2017 |
| WO | 2017093357 | 6/2017 |
| WO | 2017149152 | 9/2017 |

(56) References Cited

FOREIGN PATENT DOCUMENTS

| WO | 2017149534 | 9/2017 |
|---|---|---|
| WO | 2017180151 | 10/2017 |
| WO | 2017185051 | 10/2017 |
| WO | 2017202953 | 11/2017 |
| WO | 2018007633 | 1/2018 |
| WO | 2018050720 | 3/2018 |
| WO | 2018083037 | 5/2018 |
| WO | 2019057857 | 3/2019 |

OTHER PUBLICATIONS

Combined Search and Examination Report for U.K. Appl. No. GB1803101.3; Date of Mailing: Aug. 7, 2018; 6 pages.
Combined Search and Examination Report for U.K. Appl. No. GB1803104.7; Date of Mailing: May 23, 2018; 10 pages.
Combined Search and Examination Report for U.K. Appl. No. GB1803106.2; Date of Mailing: Jun. 12, 2018; 6 pages.
Combined Search and Examination Report for U.K. Appl. No. GB1803107.0; Date of Mailing: Jun. 15, 2018; 9 pages.
Combined Search and Examination Report for U.K. Appl. No. GB1803110.4; Date of Mailing: Jul. 5, 2018; 10 pages.
Combined Search and Examination Report for U.K. Appl. No. GB1803111.2; Date of Mailing: Aug. 1, 2018; 10 pages.
Combined Search and Examination Report for U.K. Appl. No. GB1803113.8; Date of Mailing: Aug. 17, 2018; 8 pages.
Combined Search and Examination Report for U.K. Appl. No. GB1803116.1; Date of Mailing: Aug. 20, 2018; 8 pages.
Combined Search and Examination Report for U.K. Appl. No. GB1803120.3; Date of Mailing: Jun. 29, 2018; 7 pages.
Combined Search and Examination Report for U.K. Appl. No. GB1803122.9; Date of Mailing: Aug. 10, 2018; 7 pages.
EPO, Exam Report for European Application No. 18779325.2, mail date Oct. 31, 2022.
EPO, Exam Report for European Application No. 18779325.2, mail date Jul. 17, 2023.
Fernandez Tena, Ana et al.; "Deposition of Inhaled Particles in the Lungs", Archovos De Bronconeumolgia, 2012; 48(7) 240-246.
International Preliminary Report on Patentability for International Application No. PCT/EP2018/075967; Date of Mailing: Mar. 24, 2020; 6 pages.
International Search Report and Written Opinion of International Application No. PCT/EP2018/075697; Date of Mailing: Dec. 7, 2018; 13 pages.
International Search Report and Written Opinion of International Application No. PCT/EP2019/054288; Date of Mailing: Jun. 3, 2019; 19 pages.
International Search Report and Written Opinion of International Application No. PCT/EP2019/054290; Date of Mailing: Jun. 4, 2019; 12 pages.
International Search Report and Written Opinion of International Application No. PCT/EP2019/054291; Date of Mailing: Jun. 6, 2019; 17 pages.
International Search Report and Written Opinion of International Application No. PCT/EP2019/054292; Date of Mailing: Jun. 4, 2019; 17 pages.
International Search Report and Written Opinion of International Application No. PCT/EP2019/054297; Date of Mailing: Jun. 6, 2019; 18 pages.
International Search Report and Written Opinion of International Application No. PCT/EP2019/054298; Date of Mailing: Jun. 6, 2019; 16 pages.
International Search Report and Written Opinion of International Application No. PCT/EP2019/054304; Date of Mailing: Jun. 5, 2019; 19 pages.
International Search Report and Written Opinion of International Application No. PCT/EP2019/054307; Date of Mailing: Jun. 4, 2019; 15 pages.
International Search Report and Written Opinion of International Application No. PCT/EP2019/054309; Date of Mailing: May 31, 2019; 15 pages.
International Search Report and Written Opinion of International Application No. PCT/EP2019/054311; Date of Mailing: Jun. 5, 2019; 21 pages.
IP Office China, Office Action 1 for Chinese Application No. 201880075054, mail date Dec. 22, 2022.
IP Office Japan, Decision of Refusal for Japanese Application No. 2020-568031, mail date May 16, 2023.
IP Office Japan, Decision of Refusal for Japanese Application No. 2020-568032, mail date Jan. 9, 2024.
IP Office Japan, Reasons for Refusal for Japanese Application No. 2020-568031, mail date Dec. 12, 2023.
IP Office Japan, Reasons for Refusal for Japanese Application No. 2020-568032, mail date Jun. 6, 2023.
IP Office Japan, Reasons for Refusal of Japanese Application No. 2020-516899, mail date Aug. 16, 2023.
IP Office Japan, Reasons for Refusal of Japanese Application No. 2020-516899, mail date Jan. 17, 2023, with English translation.
IP Office Japan, Reasons for Refusal of Japanese Application No. 2020-516899, mail date May 27, 2022, English machine translation.
IP Office Japan, Reasons for Refusal of Japanese Application No. 2020-568031, mail date Jan. 4, 2023, with English translation.
IP Office Japan, Reasons for Refusal of Japanese Application No. 2020-568032, mail date Jan. 17, 2023, with English translation.
IP Office Japan, Reasons for Refusal of Japanese Application No. 2020-568033, mail date Jan. 17, 2023, with English translation.
IP Office Japan, Reasons for Refusal of Japanese Application No. 2020-568034, mail date Jan. 17, 2023, with English translation.
IP Office Korea, Office Action for Korean Application No. 20207011558, mail date May 10, 2023.
Lozano, A. et al; "High-Frequency Ultrasonic Atomisation with Pulsed Excitation"; Journal of Fluid Engineering, Nov. 2003, vol. 125, 941-945.
Sono-Tek Corporation; "Ultrasonic Atomisation Technology for Precise Coatings", at www.sono-tek.com/ultrasonic-nozzle-technology/ and downloaded May 23, 2017.
Vecellio L; "The mesh nebuliser: a recent technical innovation for aerosol delivery", Breathe, Mar. 2006, vol. 2, No. 3, pp. 253-260.

* cited by examiner

AEROSOLIZATION USING TWO AEROSOL GENERATORS

CROSS-REFERENCE TO RELATED APPLICATIONS

This application is a continuation of U.S. patent application Ser. No. 18/191,820, filed Mar. 28, 2023, which is a continuation of U.S. patent application Ser. No. 16/648,483, filed Mar. 18, 2020, now U.S. Pat. No. 11,633,556, which is a 35 USC § 371 national stage of PCT/EP2018/075697, filed Sep. 21, 2018, which claims priority from GB1715386.7 filed Sep. 22, 2017. These applications are herein incorporated by reference.

FIELD

The present invention relates to a device, system and method for the delivery of aerosols. In particular, but not exclusively, one or more embodiments in accordance with the present invention relate to the delivery of aerosols comprising different active components.

BACKGROUND

Nicotine replacement therapies are aimed at people who wish to stop smoking and overcome their dependence on nicotine. One form of nicotine replacement therapy is an inhaler or inhalator. These generally have the appearance of a plastic cigarette and are used by people who crave the behaviour associated with consumption of combustible tobacco—the so-called hand-to-mouth aspect—of smoking tobacco. An inhalator comprises a replaceable nicotine cartridge. When a user inhales through the device, nicotine is atomised or aerosolised from the cartridge and is absorbed through the mucous membranes in the mouth and throat, rather than travelling into the lungs. Nicotine replacement therapies are generally classified as medicinal products and are regulated under the Human Medicines Regulations in the United Kingdom.

In addition to passive nicotine delivery devices such as the Inhalator, active nicotine delivery devices exist in the form of electronic cigarettes. The inhaled aerosol mist or vapour typically bears nicotine and/or flavourings. In use, the user may experience a similar satisfaction and physical sensation to those experienced from combustible tobacco products, and exhales an aerosol mist or vapour of similar appearance to the smoke exhaled when using such combustible tobacco products.

A smoking-substitute device generally uses heat and/or ultrasonic agitation to vaporize/aerosolise a solution comprising nicotine and/or other flavouring, propylene glycol and/or glycerol formulation into an aerosol, mist, or vapour for inhalation. A person of ordinary skill in the art will appreciate that the term "smoking-substitute device" as used herein includes, but is not limited to, electronic nicotine delivery systems (ENDS), electronic cigarettes, e-cigarettes, e-cigs, vaping cigarettes, pipes, cigars, cigarillos, vaporizers and devices of a similar nature that function to produce an aerosol mist or vapour that is inhaled by a user. Some electronic cigarettes are disposable; others are reusable, with replaceable and refillable parts.

Smoking-substitute devices may resemble a traditional cigarette and are cylindrical in form with a mouthpiece at one end through which the user can draw the aerosol, mist or vapour for inhalation. These devices usually share several common components: a power source such as a battery, a reservoir for holding the liquid to be vaporized (often termed an e-liquid), a vaporization component such as a heater for atomizing, aerosolising and/or vaporizing the liquid and to thereby produce an aerosol, mist or vapour, and control circuitry operable to actuate the vaporization component responsive to an actuation signal from a switch operative by a user or configured to detect when the user draws air through the mouthpiece by inhaling.

The popularity and use of smoking-substitute devices has grown rapidly in the past few years.

Aspects and embodiments of the invention were devised with the foregoing in mind.

SUMMARY

According to a first aspect, there is provided An aerosol delivery device comprising: a first aerosol generator to generate a first aerosol from a first aerosol precursor and to introduce the first aerosol into a first fluid flow pathway, wherein the first aerosol is sized for pulmonary penetration; a second aerosol generator to generate a second aerosol from a second aerosol precursor and to introduce the second aerosol into a second fluid flow pathway, wherein the second aerosol is sized to inhibit pulmonary penetration; wherein the second aerosol is transmissible within at least one of: a mammalian oral cavity and a mammalian nasal cavity, and the second aerosol comprising an active component for activating at least one of: one or more taste receptors in the oral cavity and one or more olfactory receptors in the nasal cavity.

Advantageously, the second aerosol is at least one of: sized to inhibit penetration to the trachea; sized to inhibit penetration to the larynx; sized to inhibit penetration to the laryngopharynx; and sized to inhibit penetration to the oropharynx.

Advantageously, the second aerosol has a mass median aerodynamic diameter that is greater than or equal to 15 microns, in particular greater than 30 microns, more particularly greater than 50 microns, yet more particularly greater than 60 microns, and even more particularly greater than 70 microns.

Advantageously, the second aerosol has a maximum mass median aerodynamic diameter that is less than 300 microns, in particular less than 200 microns, yet more particularly less than 100 microns.

Advantageously, the first aerosol precursor comprises components such that the first aerosol comprises a pulmonary deliverable active component.

Advantageously, the first aerosol has a mass median aerodynamic diameter less than or equal to 10 microns, preferably less than 8 microns, more preferably less than 5 microns, yet more preferably less than 1 micron.

Advantageously, the first aerosol generator is configured to heat the first aerosol precursor.

Advantageously, the first aerosol generator is configured to agitate the first aerosol precursor.

Advantageously, the first fluid flow pathway further receives the first aerosols from a first aerosol inlet of the device.

Advantageously, the first aerosol inlet is configured to inject the first aerosol into the first fluid flow pathway.

Advantageously, the second fluid flow pathway further receives the second aerosol from a second aerosol inlet of the device.

Advantageously, the second aerosol inlet is configured to inject the second aerosols into the second fluid flow pathway.

Advantageously, the first fluid pathway and the second fluid flow pathway merge together.

Advantageously, the first fluid pathway and the second fluid flow pathway are contiguous.

Advantageously, the second fluid flow pathway is disposed along a longitudinal axis of the first fluid flow pathway.

Advantageously, the first fluid flow pathway is disposed proximal to a gas inlet of the device and the second fluid flow pathway is disposed proximal to an aerosol outlet of the device.

Advantageously, the second fluid flow pathway is disposed proximal to a gas inlet of the device and the first fluid flow pathway is disposed proximal to an aerosol outlet of the device.

Advantageously, the second fluid flow pathway is disposed co-axially relative to the first fluid flow pathway.

Advantageously, the second fluid flow pathway is disposed adjacent the first fluid flow pathway in a side by side relationship therewith.

Advantageously, the first fluid flow pathway is separated from the second fluid flow pathway by a wall member.

Advantageously, the first fluid flow pathway comprising a first housing to constrain the fluid flow and the second fluid flow pathway comprising a second housing to constrain the second fluid flow, the first housing to receive the first aerosol; and the second housing to receive the second aerosol.

Advantageously, the first housing comprising the first aerosol generator and/or the second housing comprising the second aerosol generator.

Advantageously, the first housing comprises a removable module of the delivery device.

Advantageously, the first housing comprises a replaceable module of the delivery device.

Advantageously, the first housing comprises a refillable module of the delivery device.

Advantageously, the second housing comprises a removable module of the delivery device.

Advantageously, the second housing comprises a replaceable module of the delivery device.

Advantageously, the second housing comprises a refillable module of the delivery device.

Advantageously, the first aerosol precursor comprises nicotine, or a nicotine derivative, or a nicotine analogue.

Advantageously, the first aerosol precursor comprises a pulmonary deliverable active component that is a free nicotine salt comprising at least one of: nicotine hydrochloride; nicotine dihydrochloride; nicotine monotartrate; nicotine bitartrate; nicotine bitartrate dihridrate; nicotine sulphate; nicotine zinc chloride monohrydrate; and nicotine salicylate.

Advantageously, the second aerosol being transmissible to activate at least one of: one or more taste receptors in the oral cavity; and one or more olfactory receptors in the nasal cavity.

Advantageously, the first aerosol generator is configured to generate the first aerosol from a first aerosol precursor comprising at least one of: glycol; polyglycol; and water.

Advantageously, the second aerosol generator is configured to introduce the second aerosol into the fluid flow pathway at a pre-set period of time following an actuation of the first aerosol generator.

Advantageously, the second fluid flow pathway comprises at least one baffle configured such that a portion of the second aerosol impinges on the baffle.

Advantageously, the aerosol inlet port is configured to introduce the second aerosol of a mass median aerodynamic diameter to inhibit pulmonary penetration.

Advantageously, the second aerosol generator comprises a Venturi aperture to dispense and aerosolise the second aerosol precursor in the second aerosol generator, wherein the second aerosol precursor is a liquid.

Advantageously, the second aerosol generator comprises a piezoelectric element to dispense and aerosolise the second aerosol precursor in the second aerosol generator, wherein the second aerosol precursor is a liquid.

Advantageously, the second aerosol generator comprises a precursor substrate for the second aerosol precursor, wherein the precursor substrate comprises a hydrophobic surface.

Advantageously, the second aerosol generator comprises a plurality of capillary tubes configured to draw the second aerosol precursor from a reservoir of second aerosol precursor to a free end of the plurality of capillary tubes.

Advantageously, the free end of the plurality of capillary tubes is hydrophobic.

Advantageously, the first aerosol is of a size suitable for deep lung penetration.

Advantageously, the first aerosol has a mass median aerodynamic diameter less than 2 μm.

Advantageously, the second fluid flow pathway terminates in a second fluid flow pathway mouthpiece.

Advantageously, the first fluid flow pathway terminates in a first fluid flow pathway mouthpiece.

Advantageously, the first and second fluid flow pathways terminate in a combination mouthpiece.

Advantageously, the combination mouthpiece comprises separate pathways corresponding to the first and second fluid flow pathways respectively.

Advantageously, the merged first and second fluid flow pathways terminate in a mouthpiece.

Advantageously, the active component comprises a physiologically active component.

According to a second aspect, a first fluid pathway housing is provided, the first fluid pathway housing being for an aerosol delivery device according to the first aspect.

Advantageously, the first fluid pathway housing comprises the first aerosol precursor.

Advantageously, the first fluid pathway housing comprises the first aerosol generator.

According to a third aspect, a second fluid pathway housing is provided, the second fluid pathway housing being for an aerosol delivery device according to the first aspect.

Advantageously, the second fluid pathway housing comprises the second aerosol precursor.

Advantageously, the second fluid pathway housing comprises the second aerosol generator.

According to a fourth aspect, a kit of parts is provided, the kits of parts being for an aerosol delivery device according to the first aspect, the kit of parts including a first fluid pathway housing according to the second aspect and a second fluid flow pathway housing according to the third aspect.

BRIEF DESCRIPTION OF THE DRAWINGS

One or more specific embodiments in accordance with aspects of the present invention will be described, by way of example only, and with reference to the following drawings in which:

FIG. 21 is a schematic illustration of a static mesh atomiser; and

FIG. 22 is a schematic illustration of a vibrating mesh atomiser.

DETAILED DESCRIPTION

Figure 1:
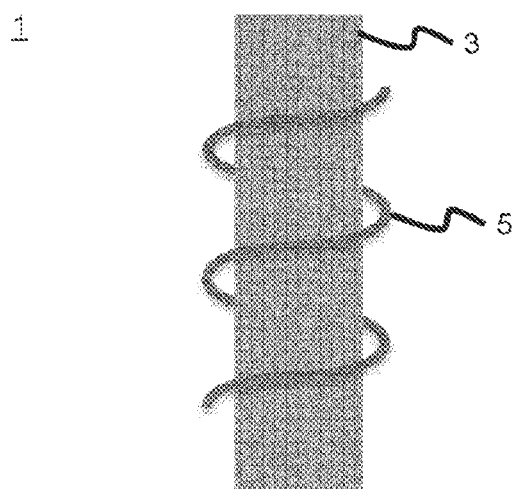
FIG. 1 is a schematic illustration of a heating element for vaping apparatus.

By way of general overview, FIG. 1 shows a schematic illustration of a vaporisation component 1 for a conventional e-cigarette. The vaporisation component comprises a wick 3, which may be solid or flexible, saturated in e-liquid with a heating coil 5 wrapped around it. Hence, the component is generally termed a wick-and-coil heater. In use, an electric current is passed through the coil 5 thereby heating the coil. This heat is transferred to the e-liquid in the wick 3 causing it to evaporate.

Figure 2:
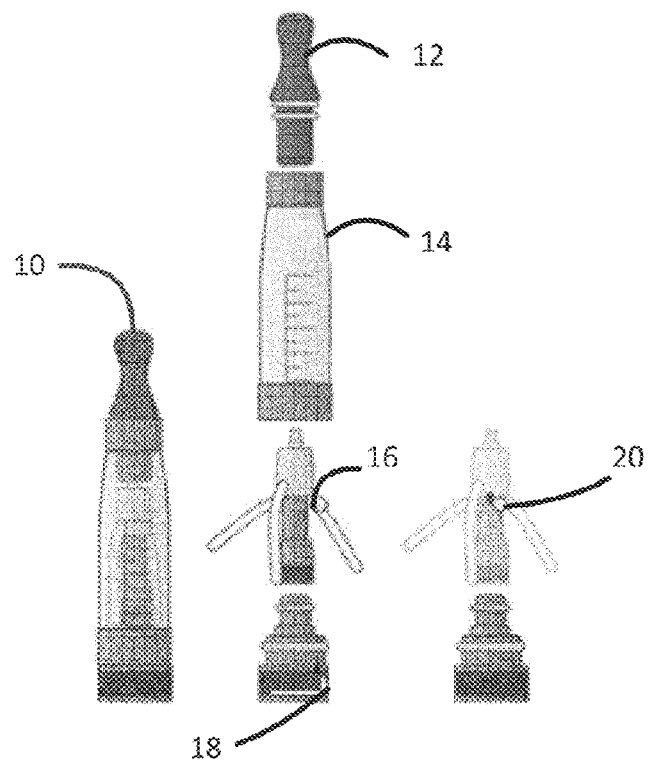
FIG. 2 is an illustration of a clearomiser vaping apparatus.

Smoking substitute devices, such as an e-cigarette, may be refillable to replace consumed e-liquid. An example of the heating, e-liquid reservoir and mouthpiece regions of an e-cigarette 10, known as a clearomiser, is illustrated in FIG. 2. The mouthpiece 12 may be coupled to the clear tank 14 which acts as a reservoir for the e-liquid. The heating arrangement includes a wick 16 which draws e-liquid to a heating element 20. The heating element 20 is powered by a battery coupled through electrical connection 18. E-liquid drawn to heating element 20 is vapourised and forms an aerosol mist which may be drawn into a user's mouth by the user drawing air through mouthpiece 12. The airflow is typically introduced through small inlets in or near the electrical connection 18 and through a central fluid pathway for the airflow which passes over or intimately adjacent the heating element such that vapourised e-liquid may be entrained in the air flow and drawn along the fluid pathway into the mouthpiece 12. Generally, the vapour condenses on the cooler air flow to form an aerosol mist of e-liquid condensate particles. The e-liquid may be flavoured. If a user wishes to change the flavour they have to change the e-liquid in their device which requires the tank for containing the e-liquid to be emptied and replaced with an e-liquid of the desired flavour. Optionally, the user may use a different device, or interchangeable tank, with the desired flavour e-liquid loaded into it.

Flavour is experienced by a user through taste and/or olfactory receptors located in their oral and nasal cavities. The inventors have recognised that flavour aerosols may penetrate into the oral and nasal cavities to deliver the flavour component to the user without penetrating any further. However, physiologically active substances such as pharmaceutical compounds and nicotine may be more effectively delivered through the pulmonary system, in particular through deep lung penetration.

Figure 3A:
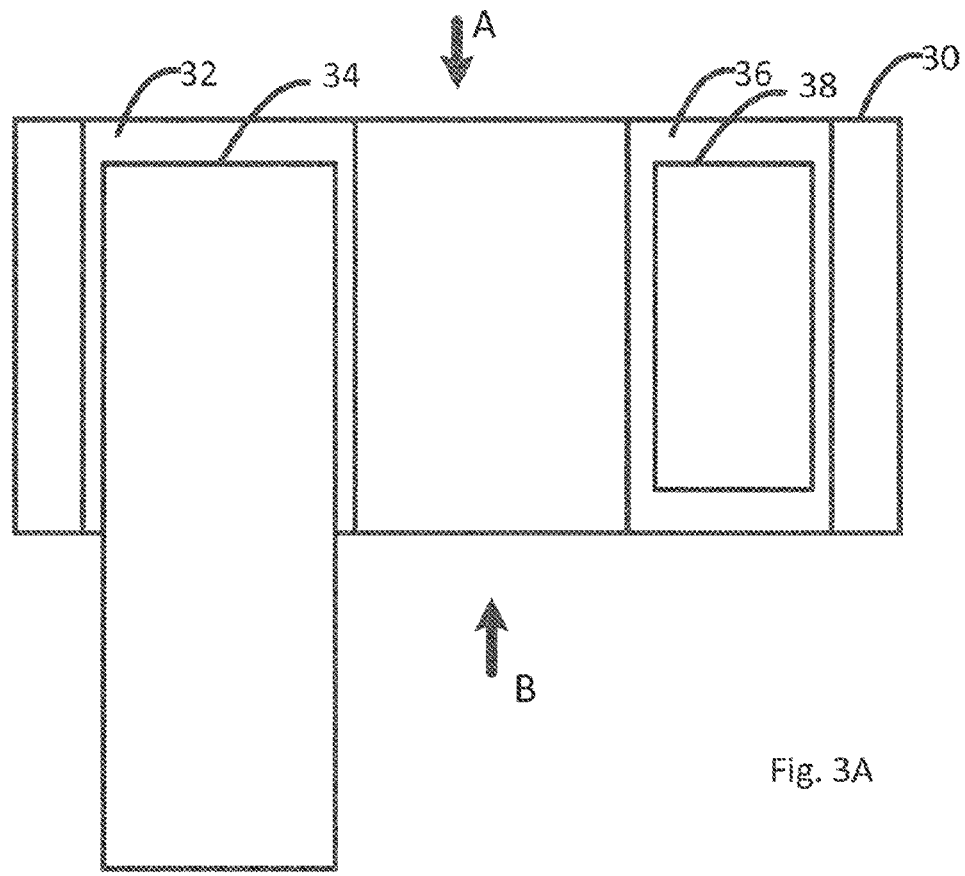
FIG. 3A is a schematic illustration of a cross-section of a mouthpiece in accordance with an embodiment of the present invention.

Turning now to FIG. 3A, there is shown a schematic illustration of a mouthpiece unit 30 which may be utilised to deliver flavour separately from an active component such as nicotine utilising a vaping apparatus. The mouthpiece 30 comprises an open-ended hollow cylindrical section 32 which is configured to receive a mouthpiece or "drip tip" 12 of a vaping unit 34 such as a clearomiser as illustrated in FIG. 2 and to provide a fluid pathway. A second open-ended hollow cylindrical section 36 is configured to receive a "flavour" element 38 and to provide a fluid pathway. The flavour element 38 is a substrate which supports a flavour component aerosol precursor typically in a liquid form such as a "Blueberry" flavour trade name FQ CO36 E-FLAVOUR BLUEBERRY supplied by Hertz Flavors GmbH & CO.KG of Reinbek, Germany. The flavour element 38 comprises a matrix to support the flavour component and through which air can be drawn from side "B" to side "A". The airflow through flavour element 38 causes aerosols of the flavour component to be formed and entrained in the airflow to be carried to side A.

A user is to place the mouthpiece 30 into their mouth with side B protruding from their mouth and to draw air to side A from side B to cause an airflow from side B through the flavour element 38 and consequently to draw flavour aerosols into the user's mouth. The user may activate the vaping apparatus 34 to generate an aerosol mist from the e-liquid precursor in the vaping apparatus by drawing air on the A side of mouthpiece 30. By activating the vaping apparatus 34 while drawing air through mouthpiece 30 a user will take both aerosols from the vaping apparatus containing an active component and flavour aerosols from flavour element 38.

Figure 3B:
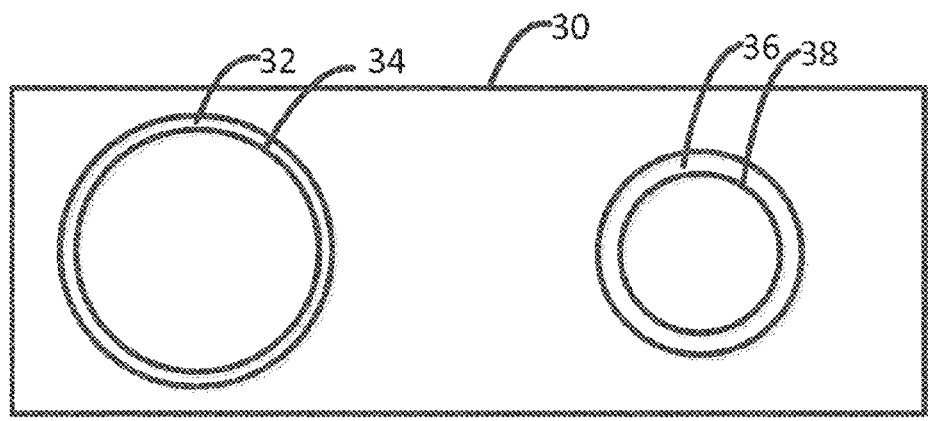
FIG. 3B is a schematic illustration of a cross-section of the mouthpiece illustrated in FIG. 3A a plane perpendicular to the plane of the cross-section illustrated in FIG. 3A.

FIG. 3B schematically illustrates mouthpiece 30 viewed from side A. Although the vaping apparatus 34 is shown to be spaced apart from the inner wall of hollow cylinder 32, that is to improve the clarity of disclosure and to clearly illustrate the respective components. In practice vaping apparatus will engage with mouthpiece 30 typically by way of a sliding friction fit. Likewise for flavour element 38 and hollow cylinder 36.

The aerosols generated in vaping apparatus 34 are formed by the heating of a vapour pre-cursor liquid such that they are typically of a size with a mass median aerodynamic diameter less than or equal to 10 microns, preferably less than 8 microns, more preferably less than 5 microns, yet more preferably less than 1 micron. Such sized aerosols tend to penetrate into a human user's pulmonary system. The smaller the aerosol the more likely it is to penetrate deeper into the pulmonary system and the more effective the transmission of the active component into the user's blood stream. Such deep lung penetration is something that is desirable for the active component but unnecessary for the flavour component. The flavour component may enter a user's oral and or nasal cavities in order to activate taste and or olfactory receptors and not penetrate the pulmonary system.

The flavour component is configured such that it is typically forms an aerosol with a mass median aerodynamic diameter that is greater than or equal to 15 microns, in particular, greater than 30 microns, more particularly greater than 50 microns, yet more particularly greater than 60 microns, and even more particularly greater than 70 microns. Without being bound by any theory, such a size of aerosol may be formed by drawing liquid droplets from a substrate at the ambient temperature of a user's environment, e.g. room temperature, by an airflow over the substrate. The size of aerosol formed without heating is typically smaller than that formed by condensation of a vapour. The size of the aerosols formed without heating such as drawing air over a substrate supporting the liquid may be influenced by the ambient temperature, the viscosity and or density of the liquid. However, it is generally, and most likely to be the case, that aerosols formed without heating are of a considerably larger size than those formed through heating. The flavour aerosols may be formed with a maximum mass median aerodynamic diameter that is less than 300 microns, in particular less than 200 microns, yet more particularly less than 100 microns. Such a range of mass median aerodynamic diameter will produce aerosols which are sufficiently small to be entrained in an airflow caused by a user drawing air through the flavour element 38 and to enter and extend through the oral and or nasal cavity to activate the taste and/or olfactory receptors.

As a brief aside, it will be appreciated that the mass median aerodynamic diameter is statistical measurement of the size of the particles/droplets in an aerosol. That is, the mass median aerodynamic diameter quantifies the size of the droplets that together form the aerosol. The mass median aerodynamic diameter may be defined as the diameter at which 50% of the particles/droplets by mass in the aerosol are larger than the mass median aerodynamic diameter and 50% of the particles/droplets by mass in the aerosol are smaller than the mass median aerodynamic diameter. The "size of the aerosol", as may be used herein, refers to the size of the particles/droplets that are comprised in the particular aerosol. The size of the particles/droplets in the aerosol may be quantified by the mass median aerodynamic diameter, for example.

The size of the aerosol generated by an aerosol generator may depend on, for example, the temperature of the liquid precursor, the density of the liquid precursor, the viscosity of the liquid precursor, or a combination. The size of the aerosol generated by an aerosol generator may also depends on the particular parameters and configuration of the aerosol generating apparatus, which are described in more detail below.

Flavour element 38 may be formed of any suitable porous material for providing the substrate. For example, it may be formed of a material typically used as a filter for a cigarette or the substrate material for a Nicorette Inhalator™, i.e. a porous polypropylene or polyethylene terephthalate. A liquid flavour component may then be dripped on to the flavour element 38. Flavour element 38 substrate may comprise a porous material where pores of the porous material hold, contain, carry, or bear a flavour compound. Optionally or additionally, the porous material may comprise a sintered material such as, for example, BioVyon™ (by Porvair Filtration Group Ltd).

In the embodiment illustrated in FIG. 4 the mouthpiece 40 is shaped to fit to a user's mouth in a conventional configuration for a mouthpiece. A tapered fluid flow pathway 42 terminates at the mouth end of piece 40 and is coupled to a cavity 44 for receiving a vaping apparatus by a fluid flow pathway 46. A cavity 58 is configured to receive a flavour pod 50 which holds a flavour element 54. The flavour pod 50 has a cavity 52 with an opening 53 sized to permit insertion of flavour element 54 into cavity 52. Cavity 52 also houses a helical spring 56. Helical spring 56 is disposed at one end of cavity 52 opposite opening 53.

Flavour element 54 is disposed in flavour pod 50 so as to rest on helical spring 56. A piezo-electric vibration unit 60 is disposed in contact with an end of flavour element 54 and is powered through electrical connection 62. Piezo-electric element 60 comprises a piezo-electric crystal electrically couplable to a power supply, such as an electrical battery, through connection 62. The piezo-electric element 60 includes a perforated membrane vibrated by a piezo-electric crystal or formed of the piezo-electric crystal itself. The perforations in the vibratable membrane form small droplets of liquid flavour component adsorbed in flavour element 54 when the membrane is vibrated. The vibration is typically in the range 100 kHz to 2.0 MHz, in particular between 108 kHz and 160 kHz, and more particularly at substantially 108 kHz, for example. Such vibration frequencies may be used to form aerosols of the liquid flavour component which may be drawn by airflow from the flavour element 54 to the terminal end of mouthpiece 50 and are of a size as set out in the ranges above.

Electrical connection 62 may be coupled to a power supply through a switch operative by a user or responsive to a pressure drop in the fluid pathway 42/cavity 58 as a user draws air from the mouthpiece 40. Optionally, electrical connection 62 may be coupled through a switch on the vape apparatus (SMP) so that the piezo-electric element 60 is actuated when a user actuates the vape apparatus.

Another configuration for apparatus which comprises separate flavour and nicotine aerosol delivery is illustrated in FIG. 11 and FIG. 12.

For the avoidance of doubt, in the following description of FIG. 11 and FIG. 12 the term "upstream" defines a position towards the point at which a fluid will be drawn into the aerosol outlet conduit 168 when the apparatus is in use, i.e. a point from which air containing aerosols is drawn into an aerosol outlet conduit 168 from atmosphere and/or from the aerosol generation unit 162. The term "downstream" defines a position from the point at which fluid containing flavour exits the flavour element 172. Based on these definitions, any fluid in the fluid passage 170 that is "upstream" of the flavour element 172 does not contain any flavour component and any fluid in the fluid passage that is "downstream" of the carrier unit 172 may contain flavour (dependent upon whether or not the flavour element 172 contains a liquid flavour component and/or a flavour compound and the extent to which the flavour component is drawn into the fluid as it traverses the carrier unit 172).

Figure 11:
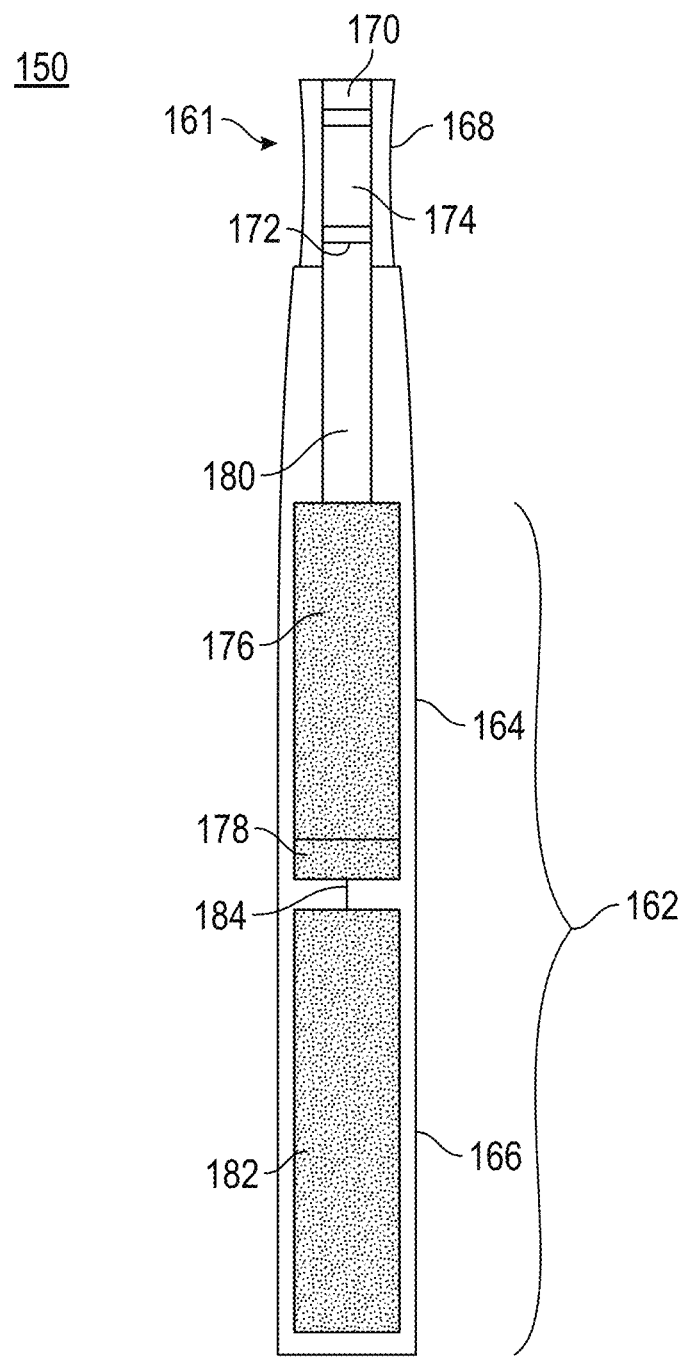
FIG. 11 is a cross-sectional side view illustration of a device in accordance with an embodiment of the present invention.

A cross-sectional side view of the apparatus 150 is schematically illustrated in FIG. 11. As can be seen in FIG. 11, the flavour element 172 contains a substrate 174, which, in one or more embodiments, is impregnated with a liquid flavour component and/or a flavour compound. Optionally, the substrate 174 may comprise a porous material where pores of the porous material hold the liquid flavour component and/or the flavour compound. Further optionally, the porous material may comprise a sintered polymer such as, for example, BioVyon™ (by Porvair Filtration Group Ltd). The porous material of substrate 174 is configured for "wicking" or "drawing" nicotine precursor material away from end regions of the substrate 14 (i.e. toward a centre region of the substrate 174). This may prevent leakage of the liquid flavour component from the substrate (and thus from the carrier unit 172 when penetrable films (not shown in FIG. 11-FIG. 12) sealing the flavour element are broken). Thus, liquid flavour component may be held within the substrate 174 until airflow therethrough (i.e. during use) causes aerosolisation and creates aerosols of flavour from the liquid flavour component.

Vaporizer portion 164 of aerosol generation unit 162 comprises a reservoir 176 configured to contain a vapour precursor material, a vaporizing arrangement 178 configured to vaporize the vapour precursor material and a fluid flow pathway passage 180 for delivery of aerosols formed from the vapour precursor material to the fluid flow pathway passage 170 of the aerosol outlet conduit 168.

The vapour precursor material may be in liquid form and may comprise one or more of glycol, polyglycol, propylene glycol and water.

The vaporizing arrangement 178 comprises a chamber (not shown) for holding vapour precursor material received from the reservoir 176 and a heating element (not shown) for heating vapour precursor material in the chamber.

The vaporizing arrangement 178 further comprises a conduit (not shown) in fluid communication with the chamber and configured to deliver aerosols formed from heated vapour precursor material in the chamber to the vapour passage 180.

The vaporizing arrangement 178 further comprises control circuitry (not shown) operative by a user, or upon detection of air and/or aerosols being drawn though the aerosol outlet conduit 168, i.e. when the user sucks or inhales.

Battery portion 166 of the aerosol creation system 162 comprises a battery 182 and a coupling 184 for mechanically and electrically coupling the battery portion 166 to the vaporizer portion 164. When the battery portion 166 and vaporizer portion 164 are coupled as shown in FIG. 11, battery 182 is electrically coupled to the vapourising arrangement 178 to supply power thereto.

Responsive to activation of the control circuitry of vaporizing arrangement 178, the heating element heats vapour precursor material in the chamber of the vaporizing arrangement 178. Vapour formed as a result of the heating process forms an aerosol of liquid condensate which passes through the conduit into the fluid pathway passage 180 of the vaporizer portion 164. This aerosol comprising fluid then passes into an upstream region of aerosol fluid pathway 170 of the aerosol outlet conduit 168, through the flavour element 172, where flavour from the substrate 174 becomes entrained in the aerosol stream, and then onwards through the downstream region of aerosol fluid pathway 170 for delivery to the user.

Figure 12:
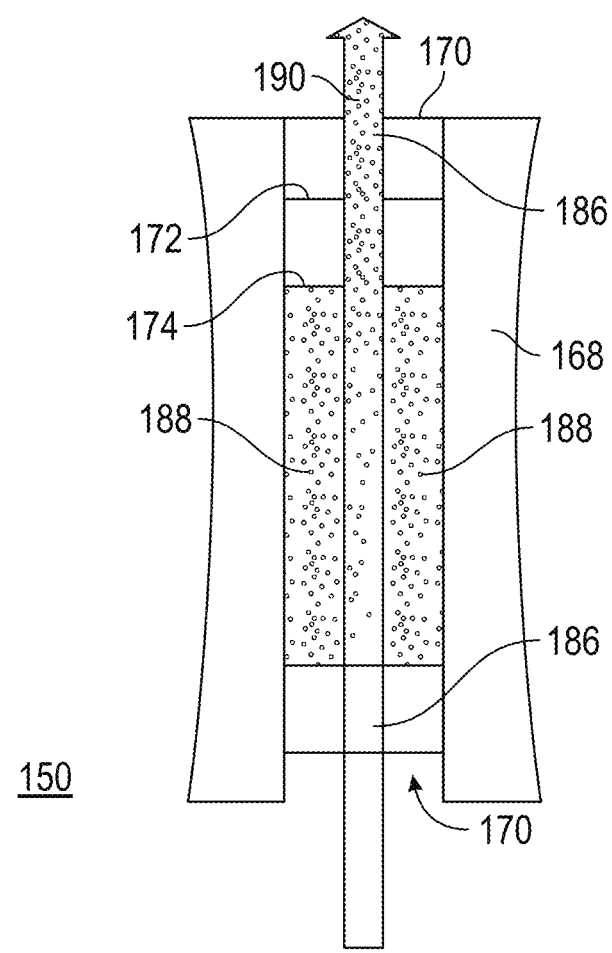
FIG. 12 is a cross-sectional side view illustration of a vapour outlet conduit of the system and device for nicotine delivery of FIGS. 1 and 2 according to one or more embodiments of the present invention.

This process is illustrated in FIG. 12, where arrow 186 schematically denotes the flow of the aerosol fluid stream from the aerosol passage of the vaporizer portion to the upstream region of aerosol fluid pathway 170 of the vapour outlet conduit 168, through the flavour element 172, and then through the downstream region of aerosol fluid pathway 170 for delivery to the user.

FIG. 12 also schematically illustrates flavour and/or flavour compounds 188 contained in the substrate 174 and the flavour and/or flavour compounds passing from the substrate 174 into the aerosol fluid stream 186, i.e. becoming entrained in the aerosol stream 186. Flavour and/or flavour compounds within the aerosol stream 186 are denoted by reference numeral 190.

Figure 4:
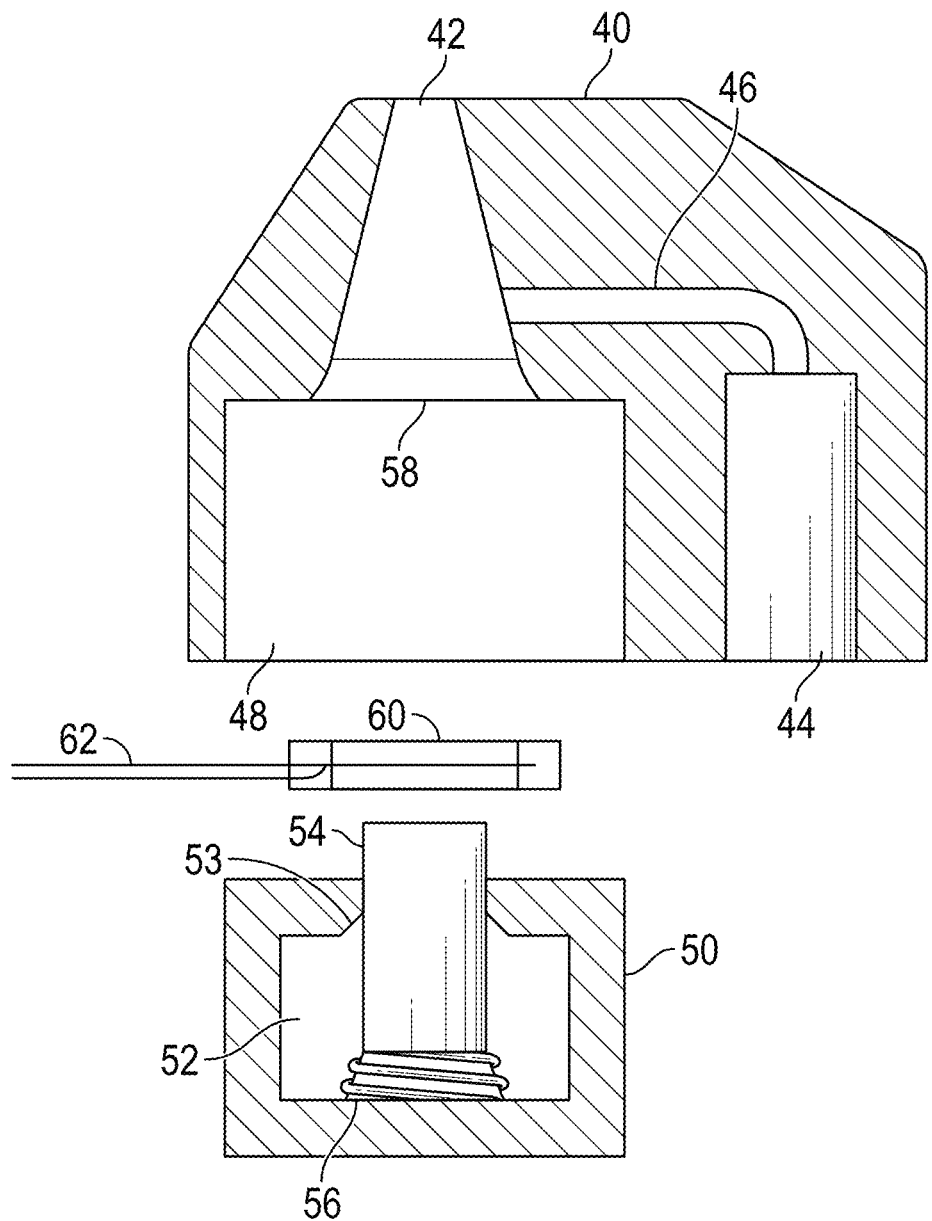
FIG. 4 is a schematic illustration of a mouthpiece in accordance with an embodiment of the present invention illustrating a piezoelectric aerosol generator.
Figure 5:
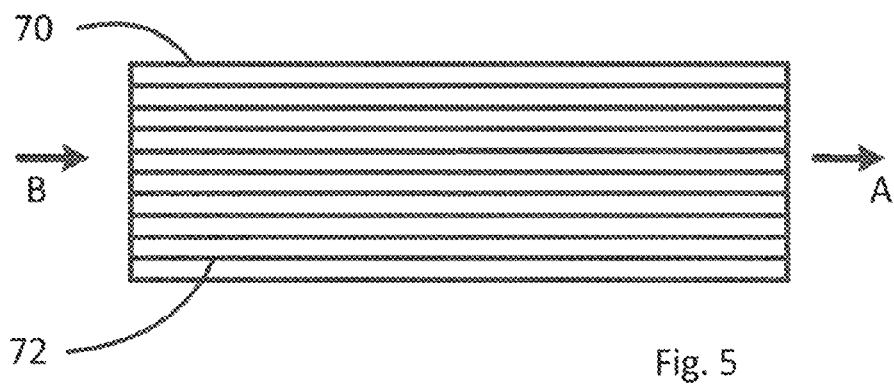
FIG. 5 is a schematic illustration of a flavour element for generating flavour aerosols in accordance with an embodiment of the present invention.

FIG. 5 is a schematic illustration of another embodiment in which a flavour element 70 provides a substrate for a liquid flavour component in which the substrate is laminar in structure having a series of laminates 72. An airflow drawn from side B traverses the laminar structures and generates an aerosol of the liquid flavour component which becomes entrained in the airflow and carried to side A to a user's mouth. A flavour element 70 may be disposed in a mouthpiece 30 such as illustrated in and described with reference to FIG. 3A and FIG. 3B or mouthpiece 40 as illustrated in and described with reference to FIG. 4.

Flavour element 70 may also be disposed in apparatus 150 in place of the flavour element 172 illustrated in FIG. 11 and FIG. 12.

Figure 6:
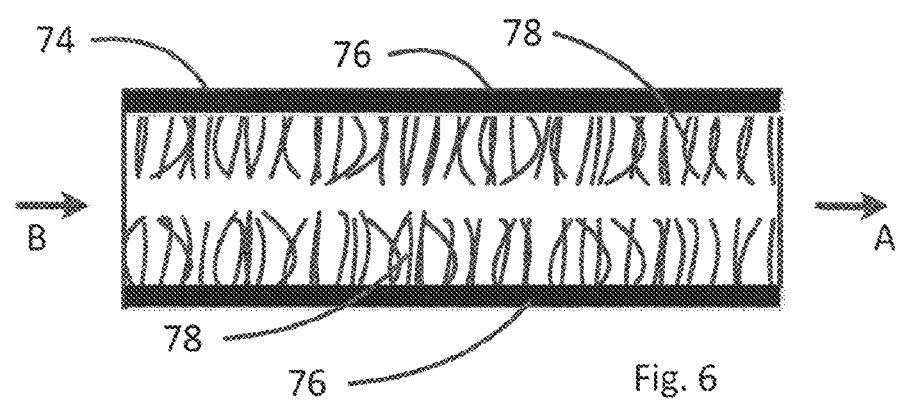
FIG. 6 is a schematic illustration of a flavour element for generating flavour aerosols in accordance with an embodiment of the present invention.

FIG. 6 is a schematic illustration of a further embodiment in which a flavour element 74 is formed of a hollow tubular section having open-ended capillary filaments 76 extending from an interior wall 78 of the tube. The capillary elements may be filled with a liquid flavour component. Air flow through the tube, illustrated by non-limiting example as from end B to end A, creates a pressure drop over a free open end of one or more of the capillary elements 76 causing droplets of the liquid flavour component to be drawn from the open end of the capillary elements and entrained in the airflow from B to A. Optionally, wall 78 may include a reservoir of liquid flavour component into which capillary filaments 76 are inserted into and or extend from to draw liquid flavour component from such a reservoir to the free open end of the capillary filaments 76. The reservoir may be a suitable matrix formed of a porous material and integrated with the wall or formed separately therefrom and inserted into the tube during assembly of the flavour element 74.

The capillary filaments are of a diameter to form aerosol-sized droplets within the ranges set out above. Generally, an open-end aperture of a diameter around the desired median diameter of the aerosol to be generated produces an aerosol of such median diameter. The exact size of the particles/droplets comprised in the aerosol will depend on the surface tension and temperature of the liquid flavour component as well as the pressure exerted on it, amongst other things. In the described embodiment the capillary filaments, or at least there open-end, are of a hydrophobic material in order to generate release of droplets of liquid.

Figure 7:
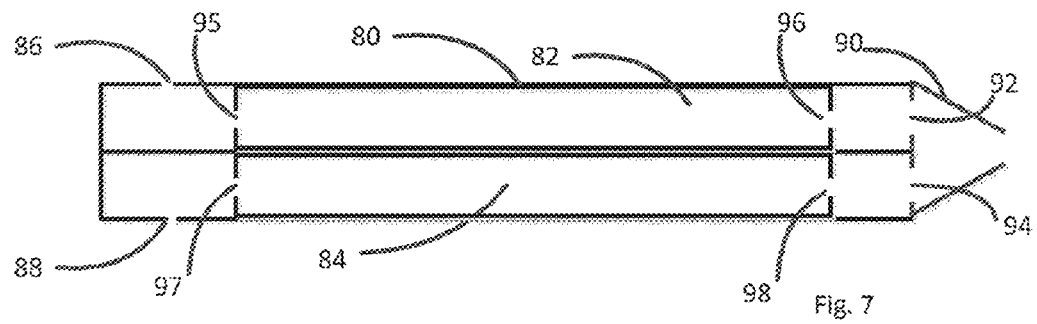
FIG. 7 is a schematic illustration of a device in accordance with an embodiment of the present invention.

In the embodiment schematically illustrated in FIG. 7 respective aerosol generators are disposed in side-by-side relationship in the apparatus 80. A flavour aerosol generator 82 and an active component aerosol generator 84 are illustrated in side-by-side relationship. Air may be drawn into flavour aerosol generator 82 from external air hole 86 and into flavour aerosol generator 82 through air hole 95. In a similar fashion air is drawn into active component generator 84 through external air hole 88 and into active component aerosol generator through air hole 97. Aerosol laden fluid exits the flavour aerosol generator 82 and active component aerosol generator 84 through outlet apertures 96 and 98 respectively. Outlet apertures 96 and 98 provide fluid communication to mouthpiece 90 through apertures 92 and 94. Mouthpiece 90 creates a plenum chamber in which the aerosols may be mixed prior to being inhaled by a user. The active component aerosol generator 84 comprises a vapour generator arrangement such as utilised in conventional vaping devices with an electrically powered heater and battery to supply electrical power. Neither details of the heater and battery pack are illustrated in the figure for convenience and clarity of disclosure.

Figure 8:
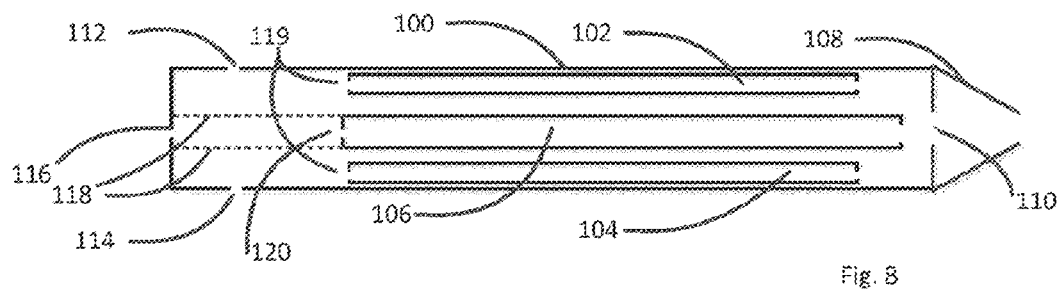
FIG. 8 is a schematic illustration of a device in accordance with an embodiment of the present invention.

A further embodiment in accordance with the present invention is schematically illustrated in FIG. 8 which shows apparatus 100 in which respective aerosol generators 102/104 and 106 are disposed in a concentric configuration. In the described embodiment flavour aerosol generator 102/104 is disposed in a concentric arrangement around the active component aerosol generator 106. Respective reference numerals 102 and 104 serve to illustrate respective parts of the flavour aerosol generator on either side of the active component aerosol generator 106 when the apparatus 100 is shown in cross-section. The apparatus has a mouthpiece 108 disposed at one end. An aperture 110 provides fluid communication from the outputs of the flavour and aerosol generators 102/104 and 106 respectively to mouthpiece 108. Air may be drawn into the aerosol generators through external air inlets 112, 114 and 116. As illustrated, a perforated conduit 118 allows air drawn in through external air inlets 112, 114 and 116 to be drawn into any one of the aerosol generators to aerosol generator airing at 119 and 120. In an optional embodiment, conduit 118 is not perforated and the respective airflow is kept apart. Likewise as for the embodiment illustrated in FIG. 7, the active component aerosol generator 106 comprises a generator as typically found in conventional vaping apparatus.

In an optional embodiment, active component aerosol generator 106 may be disposed in a circumferential arrangement about the flavour aerosol generator 102/104.

Figure 9:
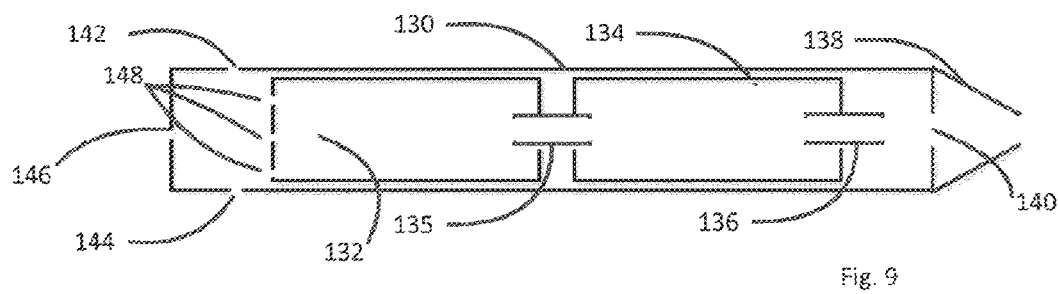
FIG. 9 is a schematic illustration of a device in accordance with an embodiment of the present invention.

FIG. 9 illustrates a yet further embodiment in accordance with the present invention in which the apparatus 130 comprises an in-line arrangement of respective active component aerosol generator 132 and flavour aerosol generator 134. The active component aerosol generator 132 is in fluid communication with the flavour aerosol generator 134 through fluid conduit 135. The fluid pathway through active component aerosol generator 132 and flavour aerosol generator 134 is coupled through fluid conduit 136 to aperture 114 and into mouthpiece 138. Air is drawn into active component aerosol generator 132 from external air inlets 142, 144 and 146 via perforations 148. Likewise as for the embodiment illustrated in FIG. 7, the active component aerosol generator 132 comprises a generator as typically found in conventional vaping apparatus.

Figure 10:
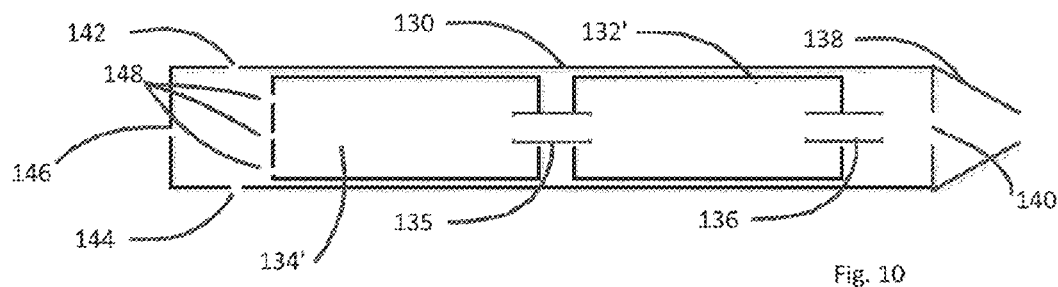
FIG. 10 is a schematic illustration of a device in accordance with an embodiment of the present invention.

In the embodiment schematically illustrated in FIG. 10, a similar arrangement is illustrated in FIG. 9 is disclosed, would like parts referred to with like numerals, but with the active component aerosol generator and flavour aerosol generator reversed. Thus, it is the flavour aerosol generator 134' that is upstream of the active component aerosol generator 132'.

The flavour aerosol generators of any of the embodiments disclosed in FIGS. 7 through to 10 may employ the flavour element configurations as disclosed in FIGS. 3 through to 6 in FIGS. 11 and 12, for example. However, any suitable aerosol generation mechanism may be employed to generate aerosols of the range defined above for the flavour aerosols.

For clarification, the active component aerosol generators in the foregoing described embodiments are configured to generate aerosols sized for pulmonary penetration, in particular deep lung penetration, and generally to generate active component aerosols sized to have a mass median aerodynamic diameter less than or equal to 10 microns, preferably less than 8 microns, more preferably less than 5 microns, yet more preferably less than 1 micron. It is the case that aerosols formed from a vapour condensate, i.e. an aerosol mist, such as occurs in a typical E-cigarette or vaping apparatus are likely to fall within the defined size ranges, or at least a significant proportion of them will fall within the defined size ranges. For example, 50% of the active component aerosols falling within the defined size ranges may be reasonably expected. It is preferable if a greater percentage falls within the defined size range, for example 75% or even higher. However, it may be acceptable to have a lower percentage such as down to 25% of the active component aerosols within the defined size ranges.

Flavour component aerosols may be generated in a number of ways of which some have been described above. The creation of aerosols (sometimes referred to as "atomisation") has been described in technical and scientific literature and such techniques may be applied, adapted to or modified for the flavour aerosol generators and elements the utilisation embodiments in accordance with the present invention. An overview of aerosolisation and techniques and methods for generating aerosols will now be provided. For the avoidance of doubt, references to droplet or particle are also references to aerosols may comprise a droplet such as a vapour condensate and/or a solid particle.

Figure 13:
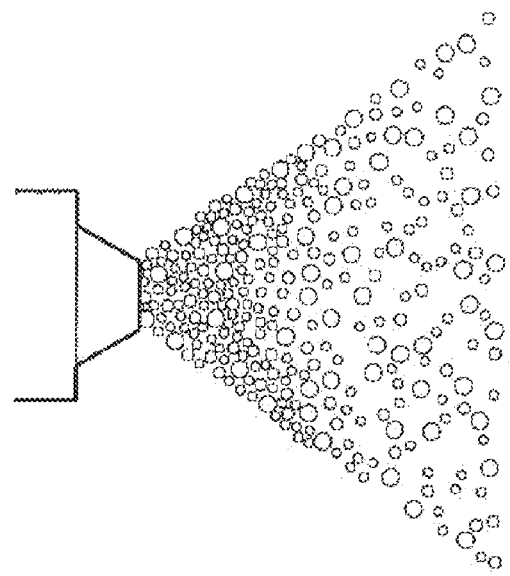
FIG. 13 is a schematic illustration of an atomiser.

Aerosols are formed initially from atomisation or from the condensing of vapour. Atomisation is the process of breaking up bulk fluids into droplets or particles. The process of breaking up the bulk fluids into a spray or aerosol that carries particles is commonly achieved using a so-called atomizer. Common examples of atomizers include shower heads, perfume sprays, and hair or deodorant sprays. FIG. 13 is a schematic illustration of a typical atomiser and the range of particle sizes produced therefrom.

An aerosol is a collection of moving particles that are the result of atomization; for most non-naturally occurring applications of atomization the aerosol moves the particles in a controlled fashion and direction. Typically, for most everyday applications the aerosol comprises a range of particle sizes depending upon various intrinsic and environmental parameters as discussed below.

A droplet or particle of fluid has a more or less spherical shape due to the surface tension of the fluid. The surface tension causes sheets or ligaments of fluid to be unstable; i.e. to break up into particles and/or atomize. As a general rule, as the temperature of the fluid increases its surface tension tends to correspondingly decrease.

A variety of properties and factors affect the size of the droplets or particles and how easily the fluid may be atomized after being ejected from an aperture; these include surface tension, viscosity, and density.

Surface Tension: surface tension tends to stabilize a fluid preventing it from separating into droplets of particles. Fluids with a higher surface tension tend to produce droplets or particles with a larger average droplet size or diameter upon atomization.

Figure 14:
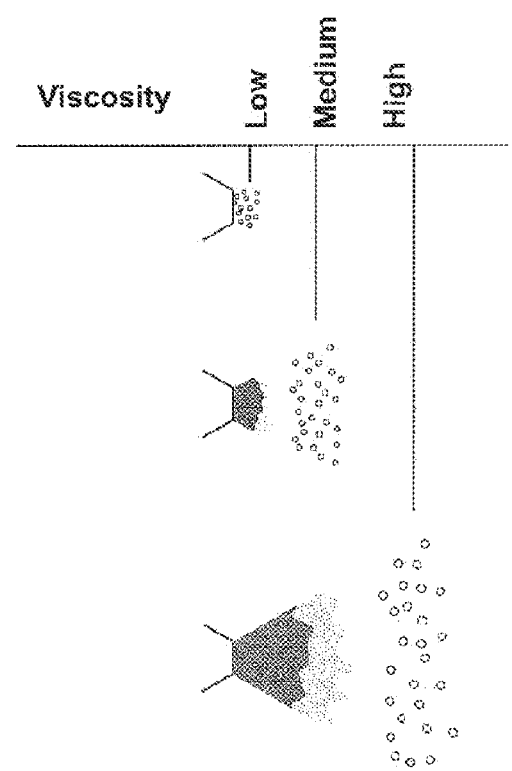
FIG. 14 is a graphical illustration of the variation of aerosol size with viscosity of precursor liquid.

Viscosity: the viscosity of a fluid has a similar effect on the size or diameter of the droplet or particle formed during atomization as surface tension. The viscosity of fluid resists agitation preventing the bulk fluid from breaking into droplets or particles. Consequently, fluids with a higher viscosity tend to produce droplets or particles with a larger average droplet size or diameter upon atomization. FIG. 14 graphically illustrates the relationship between viscosity and droplet size when atomization occurs and aerosols formed.

Density: density causes the fluid to resist acceleration. Consequently, once again fluids with a higher density tend to produce droplets or particles with a larger average droplet size or diameter upon atomization.

Atomization Processes

The process of atomisation, i.e. the process that may lead to the formation of aerosols, may take a number of different forms.

A. Pressure Atomization

Figure 15:
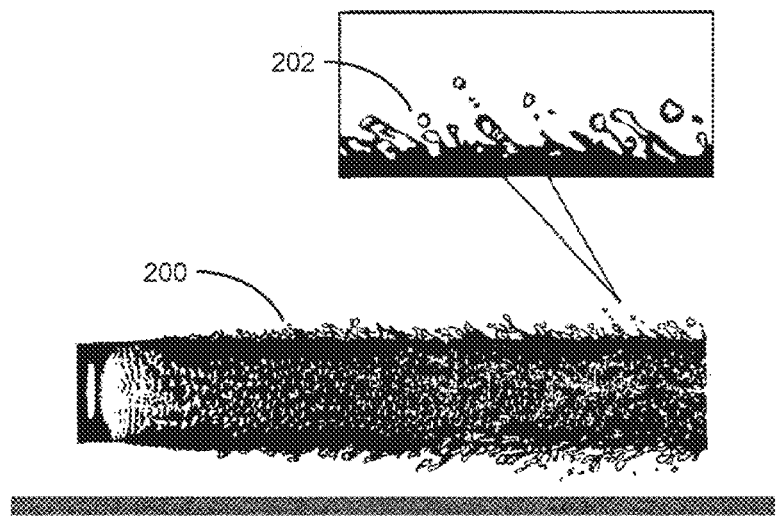
FIG. 15 is an illustration of aerosol formation from a high velocity liquid jet.

Also known as airless, air-assisted airless, hydrostatic, and hydraulic atomization, the pressure atomization process involves forcing fluid through a small nozzle or orifice at high pressure so that the fluid is ejected at high speed as a solid stream or sheet. The friction between the fluid and air disrupts the stream, causing it to break into fragments initially and ultimately into droplets. FIG. 15 schematically illustrates a high-velocity water jet 200 that breaks up into droplets 202 in an airless atomization system. In such a system a high-velocity water jet is expelled from a suitable aperture.

A number of factors affect the stream and droplet size including the diameter of the orifice, the external atmosphere (temperature and pressure), and the relative velocity of the fluid and air. As a general rule, the larger the diameter of the nozzle orifice, the larger the average droplet diameter in the spray.

The external atmosphere resists the spray and tends to break up the stream of fluid; this resistance tends to partially overcome the surface tension, viscosity and density of the fluid.

Figure 16:
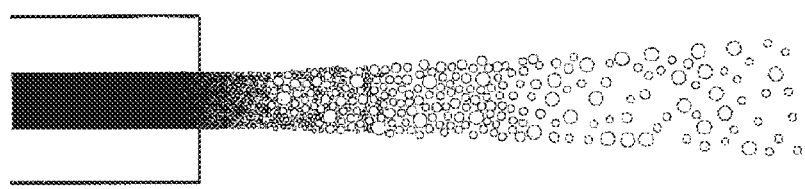
FIG. 16 is a schematic illustration of aerosol formation from a pressurised fluid exiting an aperture.

The relative velocity between the fluid and air has the greatest influence on the average diameter of the droplets in the aerosol. Since the velocity of the fluid ejected through the nozzle orifice is dependent upon pressure, as fluid pressure in the nozzle increases the average diameter of the droplets correspondingly decreases. Conversely, as fluid pressure decrease, the velocity is lower and the average diameter of the droplets increases. FIG. 16 schematically illustrates an airless atomization process in which pressurized fluid is ejected from a circular orifice into the atmosphere.

B. Air Atomization

Figure 17:
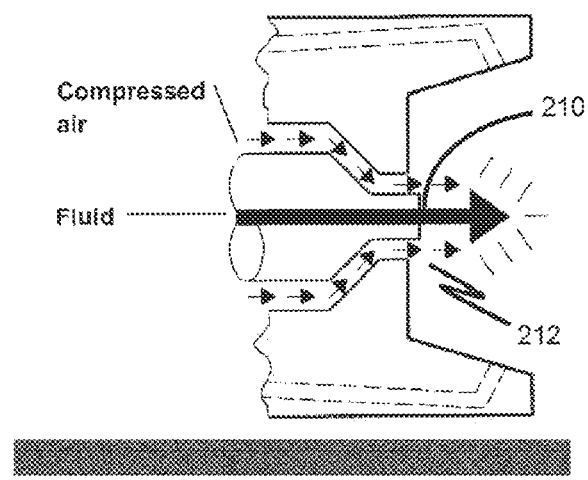
FIG. 17 is a schematic illustration of a device for air atomisation.

In air atomization, fluid is ejected from a nozzle orifice 210 at relatively low speed and low pressure and is surrounded by a high-velocity stream of air 212. Friction between the fluid and air accelerates and disrupts the fluid stream and causes atomization. As the principal energy source for atomization is air pressure, the fluid flow rate can be regulated independently of the energy source. Accordingly, air atomization has been adopted as the principal technology for atomization in medical inhalation and device technologies. FIG. 17 schematically illustrates such an arrangement with a stream of fluid passing through an orifice in which as the stream of fluid emerges, a high-speed stream of air surrounds the fluid stream.

C. Centrifugal Atomization

Figure 18:
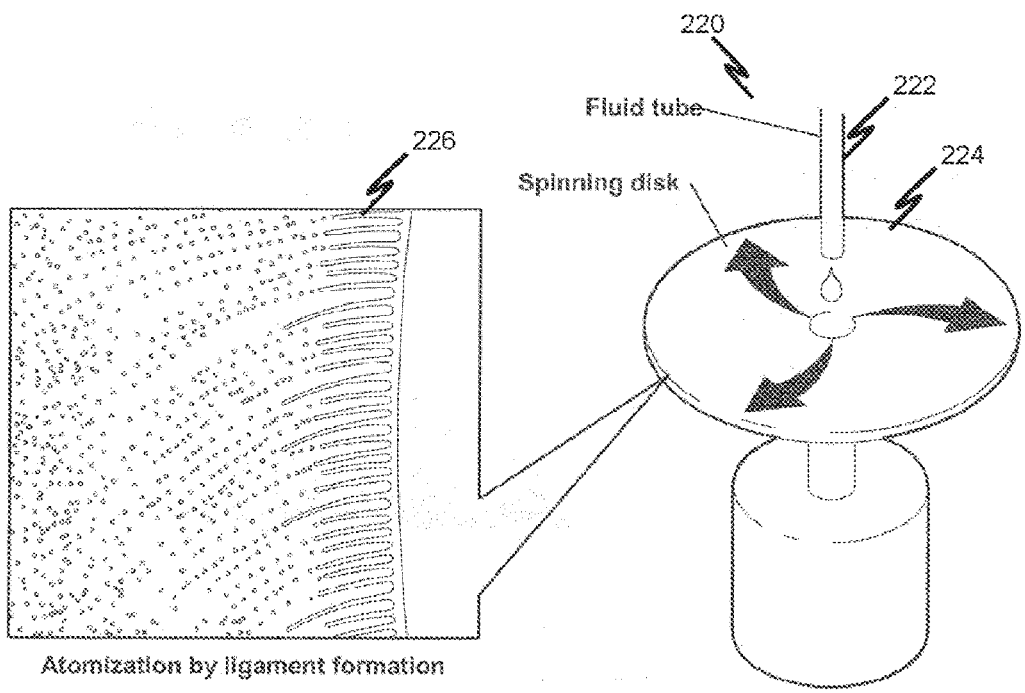
FIG. 18 is a schematic illustration of a centrifugal atomiser.

FIG. 18 schematically illustrates a centrifugal or rotary atomization system 220 (also known as rotary atomization). A nozzle 222 introduces fluid in the centre of a spinning disk 224 or cone. Centrifugal forces carry the fluid to the edge of the disk or cone. As it is ejected from the edge of the disk or cone the liquid forms ligaments 226 or sheets that break the bulk liquid into droplets or particles.

At the same rotational speed, at a low fluid flow rates droplets form closer to the edge of the disk than with higher flow rates. The fluid is ejected from the edge of the disk and moves radially away from the disk in all directions (i.e. 360°). Accordingly, where the droplets may be entrained in a directional air flow or shaping bell to cause the aerosol to travel in an axial direction.

Both the flow rate of the fluid introduced onto the spinning disk or cone, and the disk speed can be controlled independently of each another.

D. Ultrasonic Atomization

Ultrasonic atomization relies on an electromechanical device that vibrates at high frequency. The high-frequency oscillation causes fluid passing over or through the vibrating surface to break into droplets.

There are a number of types of ultrasonic nebulisers including ultrasonic wave atomizers and vibrating mesh atomizers.

a. Ultrasonic Wave Atomizers

Figure 19:
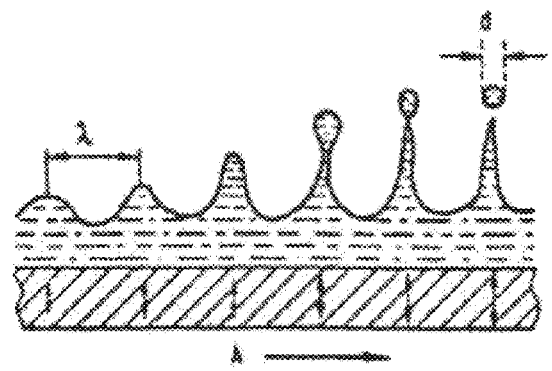
FIG. 19 is a schematic illustration of aerosol formation in an ultrasonic atomisation.

A thin layer of liquid is deposited on the surface of a resonator (typically a resonating surface connected to a piezo-electric element) which is then mechanically vibrated at high-frequency along direction A. The vibrations cause a pattern of standing capillary waves having a standing wavelength $\lambda$ when the vibration amplitude exceeds a threshold value. Upon increasing the vibration amplitude above the threshold ligament break-up of the liquid occurs and droplets are expelled from the crests/peaks of the capillary waves. FIG. 19 schematically illustrates the principles of operation of an ultrasonic atomization system.

Figure 20:
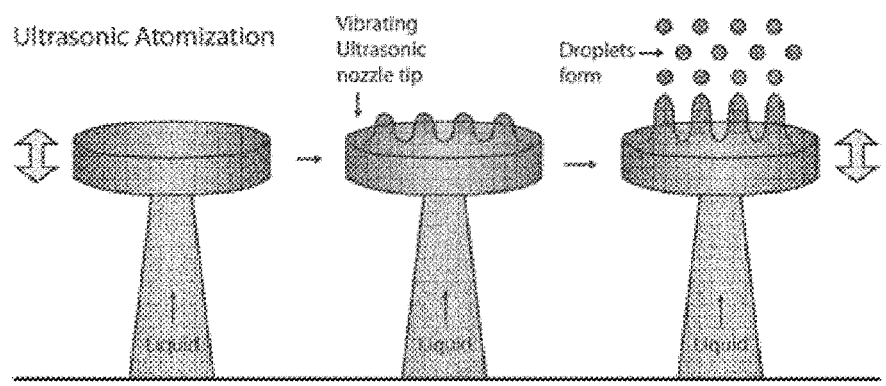
FIG. 20 is a schematic illustration of a structure for ultrasonic atomisation.

As schematically illustrated in FIG. 20, disc-shaped ceramic piezo-electric transducers or resonators convert electrical energy into mechanical energy. The transducers receive an electrical input in the form of a high-frequency signal from a power generator and convert it into vibratory motion at the same frequency. Two titanium cylinders magnify the motion and increase the vibration amplitude of the atomizing surface.

The nozzle is designed so that excitation of the piezoelectric crystal comprised in the transducer create a standing wave along the length of the nozzle. The ultrasonic energy from the crystals located in the large diameter of the nozzle body undergoes a step transition and amplification as the standing wave as it traverses the length of the nozzle.

Since the wavelength is dependent upon operating frequency, nozzle dimensions are governed by frequency. In general, high-frequency nozzles are smaller, create smaller droplets, and consequently have a smaller maximum flow capacity than nozzles that operate at lower frequencies.

The nozzle is preferably fabricated from titanium because of its good acoustical properties, high tensile strength, and excellent corrosion resistance. Liquid is introduced onto the atomizing surface through a feed tube running the length of the nozzle that absorbs some of the vibrational energy, setting up a wave motion in the liquid on the surface. For the liquid to atomize, the vibrational amplitude of the atomizing surface must be carefully controlled. Below the so called critical amplitude, the energy is insufficient to produce atomized droplets and if the amplitude is excessively high the liquid is ripped apart and 'chunks' of fluid are ejected (a condition known as "cavitation").

Since the ultrasonic atomization relies only on liquid being introduced onto the atomizing surface, the rate at which liquid is atomized depends solely on the rate at which it is delivered to the surface.

Ultrasonic wave atomizers are particularly suited to low pressure/low velocity applications and provide an aerosol spray that is highly controllable. Accordingly, since the atomization process is not reliant upon fluid pressure the volume of liquid that is atomized can be controlled by the liquid delivery system and can range from a few microliters upwards. In addition the aerosol spray can be precisely controlled and shaped by entraining the low-velocity aerosol spray in an ancillary air stream to produce a spray pattern that is as small as around 1.8 mm wide.

Furthermore, droplets produced by ultrasonic vibration have a relatively narrow average diameter distribution. Median droplet sizes range from 18-68 microns, depending upon the operating frequency of the nozzle. For example, Sono-tek claim that their ultrasonic spray nozzles can produce a median droplet diameter of around 40 microns with 99.9% of the droplets having a diameter falling in the range 5-200 microns.

b. Static Mesh Atomization

Figures 21, 22:
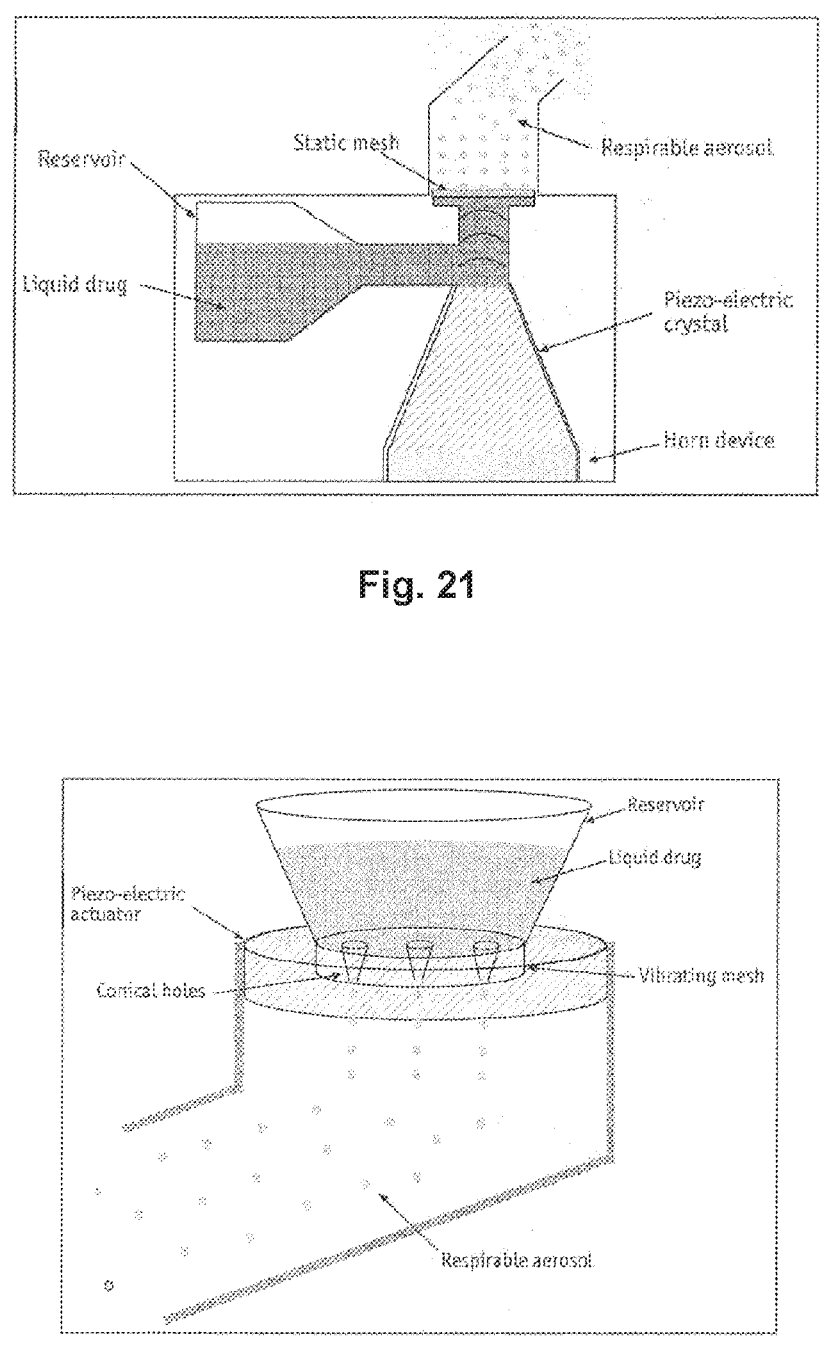

Static mesh atomizers apply a force to the liquid to force it through a static mesh as shown in FIG. 21. An ultrasonic transducer is used to generate vibrations in the liquid and push the droplets through the static mesh.

c. Vibrating Mesh Atomization

Vibrating mesh atomisers use mesh deformation or vibration to push liquid through the mesh as schematically shown in FIG. 22. Typically, an annular piezo-electric element that is contact with the mesh is used to produce vibrations around the mesh. Holes in the mesh have a conical structure, with the largest cross-section of the cone in contact proximal to the liquid reservoir. The face of the mesh deforms towards the liquid reservoir thus pumping liquid into and loading the holes with liquid. The deformation of the face on the other side of the mesh ejects droplets through the holes.

The size of the droplet and aerosol produced is dependent on the size of the holes in the mesh and the physiochemical properties of the liquid. However, one of the drawbacks to vibrating mesh devices is the potential for the holes in the mesh to clog particularly with solutions that are too viscous to pass through the mesh.

More detail concerning the various techniques for generating aerosols via atomisation may be found in the following publications.

"Deposition of Inhaled Particles in the Lungs", Ana Fernandez Tena, Pere Casan Clara; ARCHOVOS DE BRONCONEUMOLGIA, 2012; 48 (7) 240-246.

"The mesh nebuliser: a recent technical innovation for aerosol delivery", L. Vecellio; breathe, March 2006, Volume 2, No. 3, pp 253-260.

"Ultrasonic Atomisation Technology for Precise Coatings", Sono-Tek Corporation at www.sono-tek.com/ultrasonic-nozzle-technology/and downloaded 23 May 2017.

"High-Frequency Ultrasonic Atomisation with Pulsed Excitation", A. Lozano, H. Amaveda, F. Barreras, X. Jorda, M. Lozano; Journal of Fluid Engineering, November 2003, Vol. 125, 941-945.

"Swirl, T-Jet and Vibrating-Mesh Atomisers", M. Eslamian, Nasser Ashgriz; ResearchGate; www.researchgate.net/publications/251220009, December 2011.

The techniques, methods and processes for atomising liquids to generate aerosols described above may be adapted or modified for use in one or more embodiments in accordance with the present invention.

In view of the foregoing description it will be evident to a person skilled in the art that various modifications may be made within the scope of the invention. For example, the helical spring of FIG. 4 may be a leaf spring or other resiliently deformable component such as a rubber bung.

The terms "fluid", "fluid flow", "air" and "airflow" refer to any suitable fluid composition, including but not limited to a gas or a gas mixed with an atomized, volatilized, nebulized, discharged, or otherwise gaseous phase or aerosol form of an active component.

The term "active component" includes "physiologically active" or "biologically active" and to comprise any single chemical species or combination of chemical species having desirable properties for enhancing an inhaled aerosol that is suitable for adsorption upon or absorption into media suitable for use in the present invention. Furthermore, a functional component in non-liquid form, which may for example be crystalline, powdered or otherwise solid, may be substituted for a functional component without departing from the scope of the invention.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention. This description should be read to include one or at least one and the singular also includes the plural unless it is obvious that it is meant otherwise.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The following numbered clauses contain statements of broad combinations of technical features in accordance with various aspects of devices and methods disclosed herein:

1. An aerosol delivery device comprising:
    a first aerosol generator to generate a first aerosol from
        a first aerosol precursor and to introduce said first aerosol into a first fluid flow pathway, wherein said first aerosol is sized for pulmonary penetration;
a second aerosol generator to generate a second aerosol from a second aerosol precursor and to introduce the second aerosol into a second fluid flow pathway, wherein the second aerosol is sized to inhibit pulmonary penetration;
wherein the second aerosol is transmissible within at least one of: a mammalian oral cavity and a mammalian nasal cavity, and the second aerosol comprising an active component for activating at least one of: one or more taste receptors in said oral cavity and one or more olfactory receptors in said nasal cavity.

2. An aerosol delivery device according to clause 1, wherein the second aerosol is at least one of:
sized to inhibit penetration to the trachea;
sized to inhibit penetration to the larynx;
sized to inhibit penetration to the laryngopharynx; and
sized to inhibit penetration to the oropharynx.

3. An aerosol delivery device according to clause 1 or clause 2, wherein the second aerosol has a mass median aerodynamic diameter that is greater than or equal to 15 microns, in particular greater than 30 microns, more particularly greater than 50 microns, yet more particularly greater than 60 microns, and even more particularly greater than 70 microns.

4. An aerosol delivery device according to any preceding clause, wherein the second aerosol has a maximum mass median aerodynamic diameter that is less than 300 microns, in particular less than 200 microns, yet more particularly less than 100 microns.

5. An aerosol delivery device according to any of clause 1 to clause 4, wherein said first aerosol precursor comprises components such that the first aerosol comprises a pulmonary deliverable active component.

6. An aerosol delivery device according to clause 5, wherein the first aerosol has a mass median aerodynamic diameter less than or equal to 10 microns, preferably less than 8 microns, more preferably less than 5 microns, yet more preferably less than 1 micron.

7. An aerosol delivery device according to any preceding clause, wherein said first aerosol generator is configured to heat said first aerosol precursor.

8. An aerosol delivery device according to any preceding clause, wherein said first aerosol generator is configured to agitate said first aerosol precursor.

9. An aerosol delivery device according to any preceding clause, wherein said first fluid flow pathway further receives said first aerosols from a first aerosol inlet of said device.

10. An aerosol delivery device according to clause 9, wherein said first aerosol inlet is configured to inject said first aerosol into said first fluid flow pathway.

11. An aerosol delivery device according to any preceding clause, wherein said second fluid flow pathway further receives said second aerosol from a second aerosol inlet of said device.

12. An aerosol delivery device according to clause 11, wherein said second aerosol inlet is configured to inject said second aerosols into said second fluid flow pathway.

13. An aerosol device according to any preceding clause, said first fluid pathway and said second fluid flow pathway merge together.

14. An aerosol device according to preceding clause, wherein said first fluid pathway and said second fluid flow pathway are contiguous.

15. An aerosol delivery device according to clause 14, wherein said second fluid flow pathway is disposed along a longitudinal axis of said first fluid flow pathway.

16. An aerosol delivery device according to clause 14 or clause 15, wherein said first fluid flow pathway is disposed proximal to a gas inlet of said device and said second fluid flow pathway is disposed proximal to an aerosol outlet of said device.

17. An aerosol delivery device according to clause 14 or clause 15, wherein said second fluid flow pathway is disposed proximal to a gas inlet of said device and said first fluid flow pathway is disposed proximal to an aerosol outlet of said device.

18. An aerosol delivery device according to clause 12, wherein said second fluid flow pathway is disposed co-axially relative to said first fluid flow pathway.

19. An aerosol delivery device according to clause 12, wherein said second fluid flow pathway is disposed adjacent said first fluid flow pathway in a side by side relationship therewith.

20. An aerosol delivery device according to clause 18 or clause 19, wherein said first fluid flow pathway is separated from said second fluid flow pathway by a wall member.

21. An aerosol delivery device according to clause 20, said first fluid flow pathway comprising a first housing to constrain said fluid flow and said second fluid flow pathway comprising a second housing to constrain said second fluid flow, said first housing to receive said first aerosol; and said second housing to receive said second aerosol.

22. An aerosol delivery device according to clause 21, said first housing comprising said first aerosol generator and/or said second housing comprising said second aerosol generator.

23. An aerosol delivery device according to clause 21 or clause 22, wherein said first housing comprises a removable module of said delivery device.

24. An aerosol delivery device according to any of clause 21 to clause 23, wherein said first housing comprises a replaceable module of said delivery device.

25. An aerosol delivery device according to any of clause 21 to clause 24, wherein said first housing comprises a refillable module of said delivery device.

26. An aerosol delivery device according to any of clause 21 to clause 25, wherein said second housing comprises a removable module of said delivery device.

27. An aerosol delivery device according to any of clause 21 to clause 26, wherein said second housing comprises a replaceable module of said delivery device.

28. An aerosol delivery device according to any of clause 21 to clause 27, wherein said second housing comprises a refillable module of said delivery device.

29. An aerosol delivery device according to any preceding clause, wherein said first aerosol precursor comprises nicotine, or a nicotine derivative, or a nicotine analogue.

30. An aerosol delivery device according to clause 29, wherein said first aerosol precursor comprises a pulmonary deliverable active component that is a free nicotine salt comprising at least one of:
nicotine hydrochloride; nicotine dihydrochloride; nicotine monotartrate; nicotine bitartrate; nicotine bitartrate dihridrate; nicotine sulphate; nicotine zinc chloride monohrydrate; and nicotine salicylate.

31. An aerosol delivery device according to any preceding clause, said second aerosol being transmissible to activate at least one of:
    one or more taste receptors in said oral cavity; and
    one or more olfactory receptors in said nasal cavity.
32. An aerosol delivery device according to any preceding clause, wherein said first aerosol generator is configured to generate the first aerosol from a first aerosol precursor comprising at least one of:
    glycol; polyglycol; and water.
33. An aerosol delivery device according to any preceding clause, wherein said second aerosol generator is configured to introduce said second aerosol into said fluid flow pathway at a pre-set period of time following an actuation of said first aerosol generator.
34. An aerosol delivery device according to any preceding clause, wherein said second fluid flow pathway comprises at least one baffle configured such that a portion of said second aerosol impinges on said baffle.
35. An aerosol delivery device according to any preceding clause, wherein said aerosol inlet port is configured to introduce the second aerosol of a mass median aerodynamic diameter to inhibit pulmonary penetration.
36. An aerosol delivery device according to any preceding clause, wherein said second aerosol generator comprises a Venturi aperture to dispense and aerosolise the second aerosol precursor in the second aerosol generator, wherein the second aerosol precursor is a liquid.
37. An aerosol delivery device according to any of clause 1 to clause 35, wherein said second aerosol generator comprises a piezoelectric element to dispense and aerosolise the second aerosol precursor in the second aerosol generator, wherein the second aerosol precursor is a liquid.
38. An aerosol delivery device according to any of clause 1 to clause 35, wherein said second aerosol generator comprises a precursor substrate for the second aerosol precursor, wherein the precursor substrate comprises a hydrophobic surface.
39. An aerosol delivery device according to any of clause 1 to clause 35, wherein said second aerosol generator comprises a plurality of capillary tubes configured to draw the second aerosol precursor from a reservoir of second aerosol precursor to a free end of the plurality of capillary tubes.
40 An aerosol delivery device according to clause 39, wherein the free end of the plurality of capillary tubes is hydrophobic.
41. An aerosol delivery device according to any preceding clause, wherein said first aerosol is of a size suitable for deep lung penetration.
42. An aerosol delivery device according to any preceding clause, wherein said first aerosol has a mass median aerodynamic diameter less than 2 μm.
43. An aerosol delivery device according to any preceding clause dependent on clause 16 wherein said second fluid flow pathway terminates in a second fluid flow pathway mouthpiece.
44. An aerosol delivery device according to any preceding clause dependent on clause 17 wherein said first fluid flow pathway terminates in a first fluid flow pathway mouthpiece.
45. An aerosol delivery device according to any preceding clause dependent on clause 18 or clause 19 wherein said first and second fluid flow pathways terminate in a combination mouthpiece.
46. An aerosol delivery device according to clause 45 wherein said combination mouthpiece comprises separate pathways corresponding to said first and second fluid flow pathways respectively.
47. An aerosol device according to clause 13 and any of clause 14 to clause 42 dependent on clause 16, wherein said merged first and second fluid flow pathways terminate in a mouthpiece.
48. An aerosol delivery device according to any preceding clause, wherein said active component comprises a physiologically active component.
49. A first fluid flow pathway housing for an aerosol delivery device according to any preceding clause.
50. A first fluid flow pathway housing according to clause 49 comprising said first aerosol precursor.
51. A first fluid flow pathway housing according to clause 49 or clause 50 comprising said first aerosol generator.
52. A second fluid flow pathway housing for an aerosol delivery device according to any of clause 1 to clause 48.
53. A second fluid flow pathway housing according to clause 52 comprising said second aerosol precursor.
54. A second fluid flow pathway housing according to clause 52 or clause 53 comprising said second aerosol generator.
55. A kit of parts for an aerosol delivery device according to any of clause 1 to clause 48 comprising a first fluid flow pathway housing according to any of clause 49 to clause 51 and a second fluid flow pathway housing according to any of clause 52 to clause 54.

The invention claimed is:
1. An aerosol delivery device comprising:
   a first aerosol generator for generating a first aerosol from a first aerosol precursor containing a flavor component;
   a first fluid flow pathway connected to the first aerosol generator;
   a second aerosol generator for generating a second aerosol from a second aerosol liquid precursor containing an active component, the second aerosol generator converting the second aerosol liquid precursor into the second aerosol via ultrasonic aerosolization;
   a second fluid flow pathway connected to the second aerosol generator; and
   the first and second fluid flow pathways leading to a mouthpiece.
2. The aerosol delivery device of claim 1 wherein second aerosol generator comprises a piezoelectric element.
3. The aerosol delivery device of claim 2 further including a perforated membrane linked to the piezoelectric element.
4. The aerosol delivery device of claim 1 wherein the second aerosol generator is configured to introduce the second aerosol into the second fluid flow pathway at a pre-set period of time following an actuation of the first aerosol generator.
5. The aerosol delivery device of claim 1 wherein the first and second fluid flow pathways extend side-by-side and parallel to each other within a housing.
6. The aerosol delivery device of claim 1 wherein the first and second fluid flow pathways are concentric.
7. The aerosol delivery device of claim 1 wherein the first and second fluid flow pathways lead into a plenum in or adjacent to the mouthpiece.
8. An aerosol delivery device comprising:
   a first aerosol generator for generating a first aerosol from a first aerosol precursor containing a flavor component via a first ultrasonic element;

a first fluid flow pathway extending from the first aerosol generator;

a second aerosol generator for generating a second aerosol from a second aerosol precursor containing an active component via a second ultrasonic element;

a second fluid flow pathway extending from the second aerosol generator; and the first and second fluid flow pathways leading towards a mouthpiece.

9. The aerosol delivery device of claim 8 wherein at least one of the first and second ultrasonic elements comprises a piezoelectric element contacting a precursor substrate.

10. The aerosol delivery device of claim 9 further including a perforated membrane linked to the piezoelectric element.

11. The aerosol delivery device of claim 8 wherein the second aerosol generator is configured to introduce the second aerosol into the second fluid flow pathway at a pre-set period of time following an actuation of the first aerosol generator.

12. The aerosol delivery device of claim 8 wherein the first and second fluid flow pathways extend side-by-side and parallel to each other within a housing.

13. The aerosol delivery device of claim 8 wherein the first and second fluid flow pathways are concentric.

14. The aerosol delivery device of claim 8 wherein the first and second aerosol generators are arranged sequentially within a housing.

15. The aerosol delivery device of claim 8 wherein the first and second fluid flow pathways lead into a plenum in or adjacent to the mouthpiece.

16. An aerosol delivery device comprising:

first and second aerosol generators in a housing;

the first aerosol generator configured for generating a first aerosol from a first aerosol precursor;

the second aerosol generator configured for generating a second aerosol from a second aerosol precursor different from the first aerosol precursor;

first and second fluid flow pathways associated with the first and second aerosol generators, respectively, the first fluid flow pathway merging with the second fluid flow pathway in the housing; and the second aerosol generator configured to introduce the second aerosol into the second fluid flow pathway at a pre-set period of time following an actuation of the first aerosol generator.

17. The aerosol delivery device of claim 16 wherein at least one of the first and second aerosol generators comprises a piezoelectric element.

18. The aerosol delivery device of claim 16 wherein the first and second fluid flow pathways extend side-by-side and parallel to each other within a housing.

19. The aerosol delivery device of claim 16 wherein the first and second fluid flow pathways are concentric.

20. The aerosol delivery device of claim 16 wherein the first and second fluid flow pathways merge in a plenum in or adjacent to a mouthpiece.

* * * * *